United States Patent
Pacetti et al.

(10) Patent No.: US 7,632,307 B2
(45) Date of Patent: Dec. 15, 2009

(54) ABLUMINAL, MULTILAYER COATING CONSTRUCTS FOR DRUG-DELIVERY STENTS

(75) Inventors: Stephen Dirk Pacetti, San Jose, CA (US); Jessica DesNoyer, San Jose, CA (US); Yung-Ming Chen, Cupertino, CA (US); Lothar Kleiner, Los Altos, CA (US); Syed F. A. Hossainy, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 319 days.

(21) Appl. No.: 11/015,313

(22) Filed: Dec. 16, 2004

(65) Prior Publication Data

US 2006/0136048 A1 Jun. 22, 2006

(51) Int. Cl.
*A61F 2/06* (2006.01)

(52) U.S. Cl. .................................................. 623/1.44

(58) Field of Classification Search ....... 623/1.38–1.54; 427/2.1–2.22
See application file for complete search history.

(56) References Cited

U.S. PATENT DOCUMENTS

| | | | |
|---|---|---|---|
| 2,072,303 A | 3/1937 | Herrmann et al. |
| 2,386,454 A | 10/1945 | Frosch et al. |
| 2,647,017 A | 7/1953 | Coulliette |
| 2,701,559 A | 2/1955 | Cooper |
| 3,288,728 A | 11/1966 | Gorham |
| 3,687,135 A | 8/1972 | Stroganov et al. |
| 3,773,737 A | 11/1973 | Goodman et al. |
| 3,839,743 A | 10/1974 | Schwarcz |
| 3,849,514 A | 11/1974 | Gray, Jr. et al. |
| 3,900,632 A | 8/1975 | Robinson |
| 4,075,045 A | 2/1978 | Rideout |
| 4,104,410 A | 8/1978 | Malecki |
| 4,110,497 A | 8/1978 | Hoel |
| 4,132,357 A | 1/1979 | Blackinton |
| 4,164,524 A | 8/1979 | Ward et al. |
| 4,226,243 A | 10/1980 | Shalaby et al. |
| 4,321,711 A | 3/1982 | Mano |
| 4,323,071 A | 4/1982 | Simpson et al. |
| 4,329,383 A | 5/1982 | Joh |
| 4,338,942 A | 7/1982 | Fogarty |
| 4,343,931 A | 8/1982 | Barrows |

(Continued)

FOREIGN PATENT DOCUMENTS

CA 2 008 312 7/1990

(Continued)

OTHER PUBLICATIONS

U.S. Appl. No. 10/255,913, filed Sep. 26, 2002, Tang et al.

(Continued)

*Primary Examiner*—Alvin J Stewart
(74) *Attorney, Agent, or Firm*—Squire, Sanders & Dempsey, L.L.P.

(57) ABSTRACT

Embodiments of coatings for implantable medical devices, such as stents, are disclosed. The devices may include at least one structural element having an abluminal side, luminal side, and sidewalls between the abluminal and luminal sides. The coating may include at least two continuous coating layers. In some embodiments, the luminal side, and all or a majority of the sidewalls are free of at least two of the coating layers.

31 Claims, 8 Drawing Sheets

U.S. PATENT DOCUMENTS

| | | |
|---|---|---|
| 4,346,028 A | 8/1982 | Griffith |
| 4,439,185 A | 3/1984 | Lundquist |
| 4,489,670 A | 12/1984 | Mosser et al. |
| 4,516,972 A | 5/1985 | Samson et al. |
| 4,529,792 A | 7/1985 | Barrows |
| 4,538,622 A | 9/1985 | Samson et al. |
| 4,554,929 A | 11/1985 | Samson et al. |
| 4,573,470 A | 3/1986 | Fogarty |
| 4,596,574 A | 6/1986 | Urist |
| 4,599,085 A | 7/1986 | Riess et al. |
| 4,608,984 A | 9/1986 | Fogarty |
| 4,611,051 A | 9/1986 | Hayes et al. |
| 4,612,009 A | 9/1986 | Drobnik et al. |
| 4,616,593 A | 10/1986 | Kawamura et al. |
| 4,616,652 A | 10/1986 | Simpson |
| 4,629,563 A | 12/1986 | Wrasidlo |
| 4,633,873 A | 1/1987 | Dumican et al. |
| 4,638,805 A | 1/1987 | Powell |
| 4,656,083 A | 4/1987 | Hoffman et al. |
| 4,656,242 A | 4/1987 | Swan et al. |
| 4,699,611 A | 10/1987 | Bowden |
| 4,702,252 A | 10/1987 | Brooks et al. |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallstén et al. |
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,748,982 A | 6/1988 | Horzewski et al. |
| 4,768,507 A | 9/1988 | Fischell et al. |
| 4,774,039 A | 9/1988 | Wrasidlo |
| 4,776,337 A | 10/1988 | Palmaz |
| 4,800,882 A | 1/1989 | Gianturco |
| 4,816,339 A | 3/1989 | Tu et al. |
| 4,818,559 A | 4/1989 | Hama et al. |
| 4,828,561 A | 5/1989 | Woodroof |
| 4,850,999 A | 7/1989 | Planck |
| 4,865,870 A | 9/1989 | Hu et al. |
| 4,871,542 A | 10/1989 | Vilhardt |
| 4,877,030 A | 10/1989 | Beck et al. |
| 4,878,906 A | 11/1989 | Lindemann et al. |
| 4,879,135 A | 11/1989 | Greco et al. |
| 4,880,683 A | 11/1989 | Stow |
| 4,882,168 A | 11/1989 | Casey et al. |
| 4,886,062 A | 12/1989 | Wiktor |
| 4,902,289 A | 2/1990 | Yannas |
| 4,906,423 A | 3/1990 | Frisch |
| 4,931,287 A | 6/1990 | Bae et al. |
| 4,932,353 A | 6/1990 | Kawata et al. |
| 4,941,870 A | 7/1990 | Okada et al. |
| 4,943,346 A | 7/1990 | Mattelin |
| 4,950,227 A | 8/1990 | Savin et al. |
| 4,955,899 A | 9/1990 | Della Corna et al. |
| 4,967,606 A | 11/1990 | Wells et al. |
| 4,977,901 A | 12/1990 | Ofstead |
| 4,988,356 A | 1/1991 | Crittenden et al. |
| 4,994,033 A | 2/1991 | Shockey et al. |
| 4,994,298 A | 2/1991 | Yasuda |
| 4,994,560 A | 2/1991 | Kruper, Jr. et al. |
| 5,015,505 A | 5/1991 | Cetnar |
| 5,019,090 A | 5/1991 | Pinchuk |
| 5,019,096 A | 5/1991 | Fox, Jr. et al. |
| 5,028,597 A | 7/1991 | Kodama et al. |
| 5,037,392 A | 8/1991 | Hillstead |
| 5,037,427 A | 8/1991 | Harada et al. |
| 5,040,548 A | 8/1991 | Yock |
| 5,047,050 A | 9/1991 | Arpesani |
| 5,049,132 A | 9/1991 | Shaffer et al. |
| 5,053,048 A | 10/1991 | Pinchuk |
| 5,059,166 A | 10/1991 | Fischell |
| 5,059,169 A | 10/1991 | Zilber |
| 5,059,211 A | 10/1991 | Stack et al. |
| 5,062,829 A | 11/1991 | Pryor et al. |
| 5,064,435 A | 11/1991 | Porter |
| 5,078,720 A | 1/1992 | Burton et al. |
| 5,081,394 A | 1/1992 | Morishita et al. |
| 5,084,065 A | 1/1992 | Weldon et al. |
| 5,085,629 A | 2/1992 | Goldberg et al. |
| 5,087,244 A | 2/1992 | Wolinsky et al. |
| 5,087,394 A | 2/1992 | Keith |
| 5,100,429 A | 3/1992 | Sinofsky et al. |
| 5,100,992 A | 3/1992 | Cohn et al. |
| 5,102,402 A | 4/1992 | Dror et al. |
| 5,104,410 A | 4/1992 | Chowdhary |
| 5,108,416 A | 4/1992 | Ryan et al. |
| 5,108,417 A | 4/1992 | Sawyer |
| 5,108,755 A | 4/1992 | Daniels et al. |
| 5,112,457 A | 5/1992 | Marchant |
| 5,116,318 A | 5/1992 | Hillstead |
| 5,116,365 A | 5/1992 | Hillstead |
| 5,123,917 A | 6/1992 | Lee |
| 5,127,362 A | 7/1992 | Iwatsu et al. |
| 5,133,742 A | 7/1992 | Pinchuk |
| 5,134,192 A | 7/1992 | Feijen et al. |
| 5,147,370 A | 9/1992 | McNamara et al. |
| 5,156,623 A | 10/1992 | Hakamatsuka et al. |
| 5,156,911 A | 10/1992 | Stewart |
| 5,158,548 A | 10/1992 | Lau et al. |
| 5,163,951 A | 11/1992 | Pinchuk et al. |
| 5,163,952 A | 11/1992 | Froix |
| 5,163,958 A | 11/1992 | Pinchuk |
| 5,165,919 A | 11/1992 | Sasaki et al. |
| 5,167,614 A | 12/1992 | Tessmann et al. |
| 5,171,445 A | 12/1992 | Zepf |
| 5,176,638 A | 1/1993 | Don Michael |
| 5,188,734 A | 2/1993 | Zepf |
| 5,192,311 A | 3/1993 | King et al. |
| 5,197,977 A | 3/1993 | Hoffman, Jr. et al. |
| 5,205,822 A | 4/1993 | Johnson et al. |
| 5,213,561 A | 5/1993 | Weinstein et al. |
| 5,213,576 A | 5/1993 | Abiuso et al. |
| 5,219,980 A | 6/1993 | Swidler |
| 5,222,971 A | 6/1993 | Willard et al. |
| 5,225,750 A | 7/1993 | Higuchi et al. |
| 5,226,889 A | 7/1993 | Sheiban |
| 5,226,913 A | 7/1993 | Pinchuk |
| 5,229,045 A | 7/1993 | Soldani |
| 5,229,172 A | 7/1993 | Cahalan et al. |
| 5,232,444 A | 8/1993 | Just et al. |
| 5,234,456 A | 8/1993 | Silvestrini |
| 5,234,457 A | 8/1993 | Andersen |
| 5,236,447 A | 8/1993 | Kubo et al. |
| 5,242,399 A | 9/1993 | Lau et al. |
| 5,254,089 A | 10/1993 | Wang |
| 5,254,091 A | 10/1993 | Aliahmad et al. |
| 5,258,020 A | 11/1993 | Froix |
| 5,258,419 A | 11/1993 | Rolando et al. |
| 5,269,802 A | 12/1993 | Garber |
| 5,272,012 A | 12/1993 | Opolski |
| 5,278,200 A | 1/1994 | Coury et al. |
| 5,279,594 A | 1/1994 | Jackson |
| 5,282,823 A | 2/1994 | Schwartz et al. |
| 5,282,860 A | 2/1994 | Matsuno et al. |
| 5,286,254 A | 2/1994 | Shapland et al. |
| 5,289,831 A | 3/1994 | Bosley |
| 5,290,271 A | 3/1994 | Jernberg |
| 5,292,516 A | 3/1994 | Viegas et al. |
| 5,298,260 A | 3/1994 | Viegas et al. |
| 5,300,295 A | 4/1994 | Viegas et al. |
| 5,304,200 A | 4/1994 | Spaulding |
| 5,306,250 A | 4/1994 | March et al. |
| 5,306,286 A | 4/1994 | Stack et al. |

| | | | | | |
|---|---|---|---|---|---|
| 5,306,294 A | 4/1994 | Winston et al. | 5,538,493 A | 7/1996 | Gerken et al. |
| 5,306,501 A | 4/1994 | Viegas et al. | 5,545,209 A | 8/1996 | Roberts et al. |
| 5,306,786 A | 4/1994 | Moens et al. | 5,545,408 A | 8/1996 | Trigg et al. |
| 5,308,641 A | 5/1994 | Cahalan et al. | 5,551,954 A | 9/1996 | Buscemi et al. |
| 5,314,472 A | 5/1994 | Fontaine | 5,554,120 A | 9/1996 | Chen et al. |
| 5,318,531 A | 6/1994 | Leone | 5,554,182 A | 9/1996 | Dinh et al. |
| 5,328,471 A | 7/1994 | Slepian | 5,556,413 A | 9/1996 | Lam |
| 5,330,500 A | 7/1994 | Song | 5,558,642 A | 9/1996 | Schweich, Jr. et al. |
| 5,330,768 A | 7/1994 | Park et al. | 5,562,728 A | 10/1996 | Lazarus et al. |
| 5,336,518 A | 8/1994 | Narayanan et al. | 5,569,463 A | 10/1996 | Helmus et al. |
| 5,342,283 A | 8/1994 | Good | 5,571,135 A | 11/1996 | Fraser et al. |
| 5,342,348 A | 8/1994 | Kaplan | 5,571,166 A | 11/1996 | Dinh et al. |
| 5,342,395 A | 8/1994 | Jarrett et al. | 5,571,567 A | 11/1996 | Shah |
| 5,342,621 A | 8/1994 | Eury | 5,578,046 A | 11/1996 | Liu et al. |
| 5,344,426 A | 9/1994 | Lau et al. | 5,578,073 A | 11/1996 | Haimovich et al. |
| 5,344,455 A | 9/1994 | Keogh et al. | 5,584,877 A | 12/1996 | Miyake et al. |
| 5,350,800 A | 9/1994 | Verhoeven et al. | 5,588,962 A | 12/1996 | Nicholas et al. |
| 5,356,433 A | 10/1994 | Rowland et al. | 5,591,199 A | 1/1997 | Porter et al. |
| 5,360,401 A | 11/1994 | Turnland et al. | 5,591,224 A | 1/1997 | Schwartz et al. |
| 5,360,443 A | 11/1994 | Barone et al. | 5,591,227 A | 1/1997 | Dinh et al. |
| 5,364,354 A | 11/1994 | Walker et al. | 5,591,607 A | 1/1997 | Gryaznov et al. |
| 5,366,504 A | 11/1994 | Andersen et al. | 5,593,403 A | 1/1997 | Buscemi |
| 5,368,560 A | 11/1994 | Rambo et al. | 5,593,434 A | 1/1997 | Williams |
| 5,370,684 A | 12/1994 | Vallana et al. | 5,595,722 A | 1/1997 | Grainger et al. |
| 5,380,299 A | 1/1995 | Fearnot et al. | 5,599,301 A | 2/1997 | Jacobs et al. |
| 5,383,925 A | 1/1995 | Schmitt | 5,599,307 A | 2/1997 | Bacher et al. |
| 5,383,927 A | 1/1995 | DeGoicoechea et al. | 5,599,352 A | 2/1997 | Dinh et al. |
| 5,385,580 A | 1/1995 | Schmitt | 5,599,922 A | 2/1997 | Gryaznov et al. |
| 5,387,450 A | 2/1995 | Stewart | 5,605,696 A | 2/1997 | Eury et al. |
| 5,389,106 A | 2/1995 | Tower | 5,607,442 A | 3/1997 | Fischell et al. |
| 5,399,666 A | 3/1995 | Ford | 5,607,467 A | 3/1997 | Froix |
| 5,405,472 A | 4/1995 | Leone | 5,609,629 A | 3/1997 | Fearnot et al. |
| 5,409,495 A | 4/1995 | Osborn | 5,610,241 A | 3/1997 | Lee et al. |
| 5,411,466 A | 5/1995 | Hess | 5,611,775 A | 3/1997 | Machold et al. |
| 5,411,477 A | 5/1995 | Saab | 5,616,338 A | 4/1997 | Fox, Jr. et al. |
| 5,412,035 A | 5/1995 | Schmitt et al. | 5,618,298 A | 4/1997 | Simon |
| 5,415,938 A | 5/1995 | Cahalan et al. | 5,618,299 A | 4/1997 | Khosravi et al. |
| 5,417,981 A | 5/1995 | Endo et al. | 5,620,420 A | 4/1997 | Kriesel |
| 5,423,849 A | 6/1995 | Engelson et al. | 5,624,411 A | 4/1997 | Tuch |
| 5,423,885 A | 6/1995 | Williams | 5,628,730 A | 5/1997 | Shapland et al. |
| 5,429,618 A | 7/1995 | Keogh | 5,628,755 A | 5/1997 | Heller et al. |
| 5,441,515 A | 8/1995 | Khosravi et al. | 5,628,781 A | 5/1997 | Williams et al. |
| 5,443,458 A | 8/1995 | Eury et al. | 5,628,785 A | 5/1997 | Schwartz et al. |
| 5,443,496 A | 8/1995 | Schwartz et al. | 5,628,786 A | 5/1997 | Banas et al. |
| 5,443,500 A | 8/1995 | Sigwart | 5,629,077 A | 5/1997 | Turnlund et al. |
| 5,445,646 A | 8/1995 | Euteneuer et al. | 5,631,135 A | 5/1997 | Gryaznov et al. |
| 5,447,724 A | 9/1995 | Helmus et al. | 5,632,771 A | 5/1997 | Boatman et al. |
| 5,451,233 A | 9/1995 | Yock | 5,632,840 A | 5/1997 | Campbell |
| 5,455,040 A | 10/1995 | Marchant | 5,637,113 A | 6/1997 | Tartaglia et al. |
| 5,456,661 A | 10/1995 | Narciso, Jr. | 5,644,020 A | 7/1997 | Timmermann et al. |
| 5,456,713 A | 10/1995 | Chuter | 5,645,559 A | 7/1997 | Hachtman et al. |
| 5,458,615 A | 10/1995 | Klemm et al. | 5,649,951 A | 7/1997 | Davidson |
| 5,460,610 A | 10/1995 | Don Michael | 5,649,977 A | 7/1997 | Campbell |
| 5,462,990 A | 10/1995 | Hubbell et al. | 5,653,691 A | 8/1997 | Rupp et al. |
| 5,464,450 A | 11/1995 | Buscemi et al. | 5,656,080 A | 8/1997 | Staniforth et al. |
| 5,464,650 A | 11/1995 | Berg et al. | 5,656,082 A | 8/1997 | Takatsuki et al. |
| 5,470,313 A | 11/1995 | Crocker et al. | 5,658,995 A | 8/1997 | Kohn et al. |
| 5,470,603 A | 11/1995 | Staniforth et al. | 5,667,523 A | 9/1997 | Bynon et al. |
| 5,476,476 A | 12/1995 | Hillstead | 5,667,767 A | 9/1997 | Greff et al. |
| 5,476,509 A | 12/1995 | Keogh et al. | 5,667,796 A | 9/1997 | Otten |
| 5,485,496 A | 1/1996 | Lee et al. | 5,670,558 A | 9/1997 | Onishi et al. |
| 5,496,346 A | 3/1996 | Horzewski et al. | 5,674,242 A | 10/1997 | Phan et al. |
| 5,500,013 A | 3/1996 | Buscemi et al. | 5,679,400 A | 10/1997 | Tuch |
| 5,501,227 A | 3/1996 | Yock | 5,693,085 A | 12/1997 | Buirge et al. |
| 5,502,158 A | 3/1996 | Sinclair et al. | 5,693,376 A | 12/1997 | Fetherston et al. |
| 5,507,768 A | 4/1996 | Lau et al. | 5,695,498 A | 12/1997 | Tower |
| 5,511,726 A | 4/1996 | Greenspan et al. | 5,695,810 A | 12/1997 | Dubin et al. |
| 5,514,154 A | 5/1996 | Lau et al. | 5,697,967 A | 12/1997 | Dinh et al. |
| 5,514,379 A | 5/1996 | Weissleder et al. | 5,700,286 A | 12/1997 | Tartaglia et al. |
| 5,516,560 A | 5/1996 | Harayama et al. | 5,702,754 A | 12/1997 | Zhong |
| 5,516,881 A | 5/1996 | Lee et al. | 5,702,818 A | 12/1997 | Cahalan et al. |
| 5,527,337 A | 6/1996 | Stack et al. | 5,707,385 A | 1/1998 | Williams |
| 5,537,729 A | 7/1996 | Kolobow | 5,711,763 A | 1/1998 | Nonami et al. |

| Patent | Date | Inventor |
|---|---|---|
| 5,711,812 A | 1/1998 | Chapek et al. |
| 5,711,958 A | 1/1998 | Cohn et al. |
| 5,713,949 A | 2/1998 | Jayaraman |
| 5,716,981 A | 2/1998 | Hunter et al. |
| 5,718,726 A | 2/1998 | Amon et al. |
| 5,720,726 A | 2/1998 | Marcadis et al. |
| 5,721,131 A | 2/1998 | Rudolph et al. |
| 5,722,984 A | 3/1998 | Fischell et al. |
| 5,723,219 A | 3/1998 | Kolluri et al. |
| 5,725,549 A | 3/1998 | Lam |
| 5,726,297 A | 3/1998 | Gryaznov et al. |
| 5,728,068 A | 3/1998 | Leone et al. |
| 5,728,751 A | 3/1998 | Patnaik |
| 5,730,698 A | 3/1998 | Fischell et al. |
| 5,733,326 A | 3/1998 | Tomonto et al. |
| 5,733,327 A | 3/1998 | Igaki et al. |
| 5,733,330 A | 3/1998 | Cox |
| 5,733,564 A | 3/1998 | Lehtinen |
| 5,733,925 A | 3/1998 | Kunz et al. |
| 5,735,897 A | 4/1998 | Buirge |
| 5,741,554 A | 4/1998 | Tisone |
| 5,741,881 A | 4/1998 | Patnaik |
| 5,746,745 A | 5/1998 | Abele et al. |
| 5,746,998 A | 5/1998 | Torchilin et al. |
| 5,756,457 A | 5/1998 | Wang et al. |
| 5,756,476 A | 5/1998 | Epstein et al. |
| 5,759,205 A | 6/1998 | Valentini |
| 5,759,474 A | 6/1998 | Rupp et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,769,884 A | 6/1998 | Solovay |
| 5,770,609 A | 6/1998 | Grainger et al. |
| 5,772,864 A | 6/1998 | Møller et al. |
| 5,776,184 A | 7/1998 | Tuch |
| 5,780,807 A | 7/1998 | Saunders |
| 5,782,742 A | 7/1998 | Crocker et al. |
| 5,783,657 A | 7/1998 | Pavlin et al. |
| 5,788,626 A | 8/1998 | Thompson |
| 5,788,979 A * | 8/1998 | Alt et al. .............. 424/426 |
| 5,800,392 A | 9/1998 | Racchini |
| 5,800,516 A | 9/1998 | Fine et al. |
| 5,804,318 A | 9/1998 | Pinchuk et al. |
| 5,807,244 A | 9/1998 | Barot |
| 5,810,871 A | 9/1998 | Tuckey et al. |
| 5,810,873 A | 9/1998 | Morales |
| 5,811,151 A | 9/1998 | Hendriks et al. |
| 5,811,447 A | 9/1998 | Kunz et al. |
| 5,820,917 A | 10/1998 | Tuch |
| 5,823,996 A | 10/1998 | Sparks |
| 5,824,048 A | 10/1998 | Tuch |
| 5,824,049 A | 10/1998 | Ragheb et al. |
| 5,824,056 A | 10/1998 | Rosenberg |
| 5,826,586 A | 10/1998 | Mishra et al. |
| 5,830,178 A | 11/1998 | Jones et al. |
| 5,830,179 A | 11/1998 | Mikus et al. |
| 5,830,217 A | 11/1998 | Ryan |
| 5,830,461 A | 11/1998 | Billiar |
| 5,830,879 A | 11/1998 | Isner |
| 5,833,644 A | 11/1998 | Zadno-Azizi et al. |
| 5,833,651 A | 11/1998 | Donovan et al. |
| 5,833,659 A | 11/1998 | Kranys |
| 5,834,582 A | 11/1998 | Sinclair et al. |
| 5,836,962 A | 11/1998 | Gianotti |
| 5,836,965 A | 11/1998 | Jendersee et al. |
| 5,837,008 A | 11/1998 | Berg et al. |
| 5,837,313 A | 11/1998 | Ding et al. |
| 5,837,835 A | 11/1998 | Gryaznov et al. |
| 5,840,009 A | 11/1998 | Fischell et al. |
| 5,840,083 A | 11/1998 | Braach-Maksvytis |
| 5,843,033 A | 12/1998 | Ropiak |
| 5,843,119 A | 12/1998 | Schulewitz |
| 5,843,172 A | 12/1998 | Yan |
| 5,846,247 A | 12/1998 | Unsworth et al. |
| 5,849,859 A | 12/1998 | Acemoglu |
| 5,851,508 A | 12/1998 | Greff et al. |
| 5,853,408 A | 12/1998 | Muni |
| 5,854,207 A | 12/1998 | Lee et al. |
| 5,854,376 A | 12/1998 | Higashi |
| 5,855,598 A | 1/1999 | Pinchuk |
| 5,855,612 A | 1/1999 | Ohthuki et al. |
| 5,855,618 A | 1/1999 | Patnaik et al. |
| 5,857,998 A | 1/1999 | Barry |
| 5,858,556 A | 1/1999 | Eckhart et al. |
| 5,858,746 A | 1/1999 | Hubbell et al. |
| 5,858,990 A | 1/1999 | Walsh |
| 5,860,954 A | 1/1999 | Ropiak |
| 5,865,814 A | 2/1999 | Tuch |
| 5,866,113 A | 2/1999 | Hendriks et al. |
| 5,868,781 A | 2/1999 | Killion |
| 5,869,127 A | 2/1999 | Zhong |
| 5,871,436 A | 2/1999 | Eury |
| 5,871,437 A | 2/1999 | Alt |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,874,355 A | 2/1999 | Huang et al. |
| 5,876,426 A | 3/1999 | Kume et al. |
| 5,876,433 A | 3/1999 | Lunn |
| 5,876,743 A | 3/1999 | Ibsen et al. |
| 5,877,224 A | 3/1999 | Brocchini et al. |
| 5,877,263 A | 3/1999 | Patnaik et al. |
| 5,879,713 A | 3/1999 | Roth et al. |
| 5,883,011 A | 3/1999 | Lin et al. |
| 5,888,533 A | 3/1999 | Dunn |
| 5,891,192 A | 4/1999 | Murayama et al. |
| 5,893,840 A | 4/1999 | Hull et al. |
| 5,893,852 A | 4/1999 | Morales |
| 5,895,407 A | 4/1999 | Jayaraman |
| 5,897,911 A | 4/1999 | Loeffler |
| 5,897,955 A | 4/1999 | Drumheller |
| 5,898,178 A | 4/1999 | Bunker |
| 5,902,631 A | 5/1999 | Wang et al. |
| 5,902,875 A | 5/1999 | Roby et al. |
| 5,905,168 A | 5/1999 | Dos Santos et al. |
| 5,906,759 A | 5/1999 | Richter |
| 5,910,564 A | 6/1999 | Gruning et al. |
| 5,914,182 A | 6/1999 | Drumheller |
| 5,914,387 A | 6/1999 | Roby et al. |
| 5,916,234 A | 6/1999 | Lam |
| 5,916,870 A | 6/1999 | Lee et al. |
| 5,919,893 A | 7/1999 | Roby et al. |
| 5,921,416 A | 7/1999 | Uchara |
| 5,922,005 A | 7/1999 | Richter et al. |
| 5,922,393 A | 7/1999 | Jayaraman |
| 5,925,552 A | 7/1999 | Keogh et al. |
| 5,925,720 A | 7/1999 | Kataoka et al. |
| 5,928,916 A | 7/1999 | Keogh |
| 5,932,299 A | 8/1999 | Katoot |
| 5,935,135 A | 8/1999 | Bramfitt et al. |
| 5,942,209 A | 8/1999 | Leavitt et al. |
| 5,947,993 A | 9/1999 | Morales |
| 5,948,018 A | 9/1999 | Dereume et al. |
| 5,948,428 A | 9/1999 | Lee et al. |
| 5,951,881 A | 9/1999 | Rogers et al. |
| 5,954,744 A | 9/1999 | Phan et al. |
| 5,955,509 A | 9/1999 | Webber et al. |
| 5,957,975 A | 9/1999 | Lafont et al. |
| 5,958,385 A | 9/1999 | Tondeur et al. |
| 5,962,138 A | 10/1999 | Kolluri et al. |
| 5,965,720 A | 10/1999 | Gryaznov et al. |
| 5,968,091 A | 10/1999 | Pinchuk et al. |
| 5,968,092 A | 10/1999 | Buscemi et al. |

| | | | | | | |
|---|---|---|---|---|---|---|
| 5,969,422 A | 10/1999 | Ting et al. | | 6,117,979 A | 9/2000 | Hendriks et al. |
| 5,971,954 A | 10/1999 | Conway et al. | | 6,120,477 A | 9/2000 | Campbell et al. |
| 5,972,027 A | 10/1999 | Johnson | | 6,120,491 A | 9/2000 | Kohn et al. |
| 5,972,029 A | 10/1999 | Fuisz | | 6,120,535 A | 9/2000 | McDonald et al. |
| 5,972,505 A | 10/1999 | Phillips et al. | | 6,120,536 A | 9/2000 | Ding et al. |
| 5,976,155 A | 11/1999 | Foreman et al. | | 6,120,788 A | 9/2000 | Barrows |
| 5,976,182 A | 11/1999 | Cox | | 6,120,847 A | 9/2000 | Yang et al. |
| 5,980,564 A | 11/1999 | Stinson | | 6,120,904 A | 9/2000 | Hostettler et al. |
| 5,980,928 A | 11/1999 | Terry | | 6,121,027 A | 9/2000 | Clapper et al. |
| 5,980,972 A | 11/1999 | Ding | | 6,123,712 A | 9/2000 | Di Caprio et al. |
| 5,981,568 A | 11/1999 | Kunz et al. | | 6,125,523 A | 10/2000 | Brown et al. |
| 5,984,449 A | 11/1999 | Tajika et al. | | 6,126,686 A | 10/2000 | Badylak et al. |
| 5,986,169 A | 11/1999 | Gjunter | | 6,127,173 A | 10/2000 | Eckstein et al. |
| 5,997,468 A | 12/1999 | Wolff et al. | | 6,129,761 A | 10/2000 | Hubbell |
| 5,997,517 A | 12/1999 | Whitbourne | | 6,129,928 A | 10/2000 | Sarangapani et al. |
| 6,010,445 A | 1/2000 | Armini et al. | | 6,132,809 A | 10/2000 | Hynes et al. |
| 6,010,530 A | 1/2000 | Goicoechea | | 6,136,333 A | 10/2000 | Cohn et al. |
| 6,010,573 A | 1/2000 | Bowlin | | 6,139,573 A * | 10/2000 | Sogard et al. ............... 623/1.13 |
| 6,011,125 A | 1/2000 | Lohmeijer et al. | | 6,140,127 A | 10/2000 | Sprague |
| 6,013,099 A | 1/2000 | Dinh et al. | | 6,140,431 A | 10/2000 | Kinker et al. |
| 6,015,541 A | 1/2000 | Greff et al. | | 6,143,354 A | 11/2000 | Koulik et al. |
| 6,019,789 A | 2/2000 | Dinh et al. | | 6,143,370 A | 11/2000 | Panagiotou et al. |
| 6,024,918 A | 2/2000 | Hendriks et al. | | 6,149,574 A | 11/2000 | Trauthen et al. |
| 6,027,510 A | 2/2000 | Alt | | 6,150,630 A | 11/2000 | Perry et al. |
| 6,027,526 A | 2/2000 | Limon et al. | | 6,153,252 A | 11/2000 | Hossainy et al. |
| 6,030,371 A | 2/2000 | Pursley | | 4,776,337 A | 12/2000 | Palmaz |
| 6,033,582 A | 3/2000 | Lee et al. | | 6,156,373 A | 12/2000 | Zhong et al. |
| 6,033,719 A | 3/2000 | Keogh | | 6,159,227 A | 12/2000 | Di Caprio et al. |
| 6,034,204 A | 3/2000 | Mohr et al. | | 6,159,229 A | 12/2000 | Jendersee et al. |
| 6,042,606 A | 3/2000 | Frantzen | | 6,159,951 A | 12/2000 | Karpeisky et al. |
| 6,042,875 A | 3/2000 | Ding et al. | | 6,159,978 A | 12/2000 | Myers et al. |
| 6,045,899 A | 4/2000 | Wang et al. | | 6,160,084 A | 12/2000 | Langer et al. |
| 6,048,964 A | 4/2000 | Lee et al. | | 6,165,212 A | 12/2000 | Dereume et al. |
| 6,051,021 A | 4/2000 | Frid | | 6,166,130 A | 12/2000 | Rhee et al. |
| 6,051,576 A | 4/2000 | Ashton et al. | | 6,168,617 B1 | 1/2001 | Blaeser et al. |
| 6,051,648 A | 4/2000 | Rhee et al. | | 6,168,619 B1 | 1/2001 | Dinh et al. |
| 6,054,553 A | 4/2000 | Groth et al. | | 6,169,170 B1 | 1/2001 | Gryaznov et al. |
| 6,056,906 A | 5/2000 | Werneth et al. | | 6,171,609 B1 | 1/2001 | Kunz |
| 6,056,993 A | 5/2000 | Leidner et al. | | 6,172,167 B1 | 1/2001 | Stapert et al. |
| 6,059,752 A | 5/2000 | Segal | | 6,174,316 B1 | 1/2001 | Tuckey et al. |
| 6,059,810 A | 5/2000 | Brown et al. | | 6,174,330 B1 | 1/2001 | Stinson |
| 6,060,451 A | 5/2000 | DiMaio et al. | | 6,177,523 B1 | 1/2001 | Reich et al. |
| 6,060,518 A | 5/2000 | Kabanov et al. | | 6,180,632 B1 | 1/2001 | Myers et al. |
| 6,063,092 A | 5/2000 | Shin | | 6,183,505 B1 | 2/2001 | Mohn, Jr. et al. |
| 6,066,156 A | 5/2000 | Yan | | 6,187,045 B1 | 2/2001 | Fehring et al. |
| 6,071,266 A | 6/2000 | Kelley | | 6,193,727 B1 | 2/2001 | Foreman et al. |
| 6,071,305 A | 6/2000 | Brown et al. | | 6,203,551 B1 | 3/2001 | Wu |
| 6,074,659 A | 6/2000 | Kunz et al. | | 6,209,621 B1 | 4/2001 | Treacy |
| 6,080,099 A | 6/2000 | Slater et al. | | 6,210,715 B1 | 4/2001 | Starling et al. |
| 6,080,177 A | 6/2000 | Igaki et al. | | 6,211,249 B1 | 4/2001 | Cohn et al. |
| 6,080,190 A | 6/2000 | Schwartz | | 6,214,115 B1 | 4/2001 | Taylor et al. |
| 6,080,488 A | 6/2000 | Hostettler et al. | | 6,214,407 B1 | 4/2001 | Laube et al. |
| 6,083,258 A | 7/2000 | Yadav | | 6,214,901 B1 | 4/2001 | Chudzik et al. |
| 6,086,610 A | 7/2000 | Duerig et al. | | 6,217,586 B1 | 4/2001 | Mackenzie |
| 6,090,330 A | 7/2000 | Gawa et al. | | 6,217,721 B1 | 4/2001 | Xu et al. |
| 6,093,199 A | 7/2000 | Brown et al. | | 6,224,626 B1 | 5/2001 | Steinke |
| 6,093,463 A | 7/2000 | Thakrar | | 6,224,675 B1 | 5/2001 | Prentice et al. |
| 6,096,070 A | 8/2000 | Ragheb et al. | | 6,224,894 B1 | 5/2001 | Jamiolkowski et al. |
| 6,096,525 A | 8/2000 | Patnaik | | 6,228,845 B1 | 5/2001 | Donovan et al. |
| 6,099,455 A | 8/2000 | Columbo et al. | | 6,231,590 B1 | 5/2001 | Slaikeu et al. |
| 6,099,559 A | 8/2000 | Nolting | | 6,231,600 B1 | 5/2001 | Zhong |
| 6,099,561 A * | 8/2000 | Alt ............................ 623/1.44 | | 6,240,616 B1 | 6/2001 | Yan |
| 6,099,562 A | 8/2000 | Ding et al. | | 6,242,041 B1 | 6/2001 | Katoot et al. |
| 6,103,230 A | 8/2000 | Billiar et al. | | 6,245,076 B1 | 6/2001 | Yan |
| 6,106,454 A | 8/2000 | Berg et al. | | 6,245,099 B1 | 6/2001 | Edwin et al. |
| 6,106,530 A | 8/2000 | Harada | | 6,245,103 B1 | 6/2001 | Stinson |
| 6,106,889 A | 8/2000 | Beavers et al. | | 6,245,753 B1 | 6/2001 | Byun et al. |
| 6,107,416 A | 8/2000 | Patnaik et al. | | 6,245,760 B1 | 6/2001 | He et al. |
| 6,110,180 A | 8/2000 | Foreman et al. | | 6,248,129 B1 | 6/2001 | Froix |
| 6,110,188 A | 8/2000 | Narciso, Jr. | | 6,248,344 B1 | 6/2001 | Ylanen et al. |
| 6,110,483 A | 8/2000 | Whitbourne et al. | | 6,251,135 B1 | 6/2001 | Stinson et al. |
| 6,113,629 A | 9/2000 | Ken | | 6,251,136 B1 * | 6/2001 | Guruwaiya et al. ......... 623/1.46 |
| 6,117,479 A | 9/2000 | Hogan et al. | | 6,251,142 B1 | 6/2001 | Bernacca et al. |

| | | | |
|---|---|---|---|
| 6,253,443 B1 | 7/2001 | Johnson |
| 6,254,632 B1 | 7/2001 | Wu et al. |
| 6,258,099 B1 | 7/2001 | Mareiro et al. |
| 6,258,121 B1 | 7/2001 | Yang et al. |
| 6,258,371 B1 | 7/2001 | Koulik et al. |
| 6,262,034 B1 | 7/2001 | Mathiowitz et al. |
| 6,270,788 B1 | 8/2001 | Koulik et al. |
| 6,273,850 B1 | 8/2001 | Gambale |
| 6,273,913 B1 | 8/2001 | Wright et al. |
| 6,277,110 B1 | 8/2001 | Morales |
| 6,277,449 B1 | 8/2001 | Kolluri et al. |
| 6,279,368 B1 | 8/2001 | Escano et al. |
| 6,281,262 B1 | 8/2001 | Shikinami |
| 6,283,947 B1 | 9/2001 | Mirzaee |
| 6,283,949 B1 | 9/2001 | Roorda |
| 6,284,305 B1 | 9/2001 | Ding et al. |
| 6,284,333 B1 | 9/2001 | Wang et al. |
| 6,287,332 B1 | 9/2001 | Bolz et al. |
| 6,287,628 B1 | 9/2001 | Hossainy et al. |
| 6,290,721 B1 | 9/2001 | Heath |
| 6,293,966 B1 | 9/2001 | Frantzen |
| 6,294,836 B1 | 9/2001 | Paranjpe et al. |
| 6,296,603 B1 | 10/2001 | Turnlund et al. |
| 6,299,604 B1 | 10/2001 | Ragheb et al. |
| 6,303,901 B1 | 10/2001 | Perry et al. |
| 6,306,176 B1 | 10/2001 | Whitbourne |
| 6,312,459 B1 | 11/2001 | Huang et al. |
| 6,319,520 B1 | 11/2001 | Wuthrich et al. |
| 6,322,588 B1 | 11/2001 | Ogle et al. |
| 6,322,847 B1 | 11/2001 | Zhong et al. |
| 6,327,772 B1 | 12/2001 | Zadno-Azizi et al. |
| 6,331,313 B1 | 12/2001 | Wong et al. |
| 6,335,029 B1 | 1/2002 | Kamath et al. |
| 6,344,035 B1 | 2/2002 | Chudzik et al. |
| 6,346,110 B2 | 2/2002 | Wu |
| 6,358,556 B1 | 3/2002 | Ding et al. |
| 6,362,099 B1 | 3/2002 | Gandikota et al. |
| 6,364,903 B2 | 4/2002 | Tseng et al. |
| 6,375,458 B1 | 4/2002 | Moorleghem et al. |
| 6,375,826 B1 | 4/2002 | Wang et al. |
| 6,379,379 B1 * | 4/2002 | Wang ................ 623/1.15 |
| 6,379,381 B1 | 4/2002 | Hossainy et al. |
| 6,387,118 B1 | 5/2002 | Hanson |
| 6,387,121 B1 | 5/2002 | Alt |
| 6,387,379 B1 | 5/2002 | Goldberg et al. |
| 6,388,043 B1 | 5/2002 | Langer et al. |
| 6,395,325 B1 | 5/2002 | Hedge et al. |
| 6,395,326 B1 | 5/2002 | Castro et al. |
| 6,406,738 B1 | 6/2002 | Hogan et al. |
| 6,409,761 B1 | 6/2002 | Jang |
| 6,413,272 B1 | 7/2002 | Igaki |
| 6,419,692 B1 * | 7/2002 | Yang et al. .............. 623/1.15 |
| 6,420,189 B1 | 7/2002 | Lopatin |
| 6,423,092 B2 | 7/2002 | Datta et al. |
| 6,436,816 B1 | 8/2002 | Lee et al. |
| 6,444,567 B1 | 9/2002 | Besser et al. |
| 6,447,835 B1 | 9/2002 | Wang et al. |
| 6,451,373 B1 | 9/2002 | Hossainy et al. |
| 6,454,738 B1 | 9/2002 | Tran et al. |
| 6,455,424 B1 | 9/2002 | McTeer et al. |
| 6,461,632 B1 | 10/2002 | Gogolewski |
| 6,462,284 B1 | 10/2002 | Hashimoto |
| 6,464,720 B2 | 10/2002 | Boatman et al. |
| 6,468,906 B1 | 10/2002 | Chan et al. |
| 6,479,565 B1 | 11/2002 | Stanley |
| 6,481,262 B2 | 11/2002 | Ching et al. |
| 6,482,834 B2 | 11/2002 | Spada et al. |
| 6,485,512 B1 | 11/2002 | Cheng |
| 6,488,701 B1 * | 12/2002 | Nolting et al. ............. 623/1.13 |
| 6,488,773 B1 | 12/2002 | Ehrhardt et al. |
| 6,491,666 B1 | 12/2002 | Santini, Jr. et al. |
| 6,492,615 B1 | 12/2002 | Flanagan |
| 6,494,862 B1 | 12/2002 | Ray et al. |
| 6,494,908 B1 | 12/2002 | Huxel et al. |
| 6,495,156 B2 | 12/2002 | Wenz et al. |
| 6,495,200 B1 | 12/2002 | Chan et al. |
| 6,503,538 B1 | 1/2003 | Chu et al. |
| 6,503,556 B2 | 1/2003 | Harish et al. |
| 6,503,954 B1 * | 1/2003 | Bhat et al. ................ 514/772.2 |
| 6,504,307 B1 | 1/2003 | Malik et al. |
| 6,506,437 B1 | 1/2003 | Harish et al. |
| 6,510,722 B1 | 1/2003 | Ching et al. |
| 6,511,748 B1 | 1/2003 | Barrows |
| 6,517,888 B1 | 2/2003 | Weber |
| 6,517,889 B1 | 2/2003 | Jayaraman |
| 6,521,284 B1 | 2/2003 | Parsons et al. |
| 6,524,232 B1 | 2/2003 | Tang et al. |
| 6,524,347 B1 | 2/2003 | Myers et al. |
| 6,527,801 B1 | 3/2003 | Dutta |
| 6,527,863 B1 | 3/2003 | Pacetti et al. |
| 6,528,526 B1 | 3/2003 | Myers et al. |
| 6,530,950 B1 | 3/2003 | Alvarado et al. |
| 6,530,951 B1 | 3/2003 | Bates et al. |
| 6,537,589 B1 | 3/2003 | Chae et al. |
| 6,539,607 B1 | 4/2003 | Fehring et al. |
| 6,540,776 B2 | 4/2003 | Sanders Millare et al. |
| 6,540,777 B2 | 4/2003 | Stenzel |
| 6,544,223 B1 | 4/2003 | Kokish |
| 6,544,543 B1 | 4/2003 | Mandrusov et al. |
| 6,544,582 B1 | 4/2003 | Yoe |
| 6,554,758 B2 | 4/2003 | Turnlund et al. |
| 6,554,854 B1 | 4/2003 | Flanagan |
| 6,555,059 B1 | 4/2003 | Myrick et al. |
| 6,555,157 B1 | 4/2003 | Hossainy |
| 6,558,733 B1 | 5/2003 | Hossainy et al. |
| 6,562,136 B1 | 5/2003 | Chappa et al. |
| 6,565,599 B1 | 5/2003 | Hong et al. |
| 6,565,659 B1 | 5/2003 | Pacetti et al. |
| 6,569,191 B1 | 5/2003 | Hogan |
| 6,569,193 B1 | 5/2003 | Cox et al. |
| 6,572,644 B1 | 6/2003 | Moein |
| 6,572,672 B2 | 6/2003 | Yadav et al. |
| 6,574,851 B1 | 6/2003 | Mirizzi |
| 6,582,417 B1 | 6/2003 | Ledesma et al. |
| 6,585,755 B2 | 7/2003 | Jackson et al. |
| 6,585,765 B1 | 7/2003 | Hossainy et al. |
| 6,585,926 B1 | 7/2003 | Mirzaee |
| 6,592,614 B2 | 7/2003 | Lenker et al. |
| 6,592,617 B2 | 7/2003 | Thompson |
| 6,596,296 B1 | 7/2003 | Nelson et al. |
| 6,605,114 B1 | 8/2003 | Yan et al. |
| 6,605,154 B1 | 8/2003 | Villareal |
| 6,605,874 B2 | 8/2003 | Leu et al. |
| 6,610,087 B1 | 8/2003 | Zarbatany et al. |
| 6,613,072 B2 | 9/2003 | Lau et al. |
| 6,616,765 B1 | 9/2003 | Hossaony et al. |
| 6,623,448 B2 | 9/2003 | Slater |
| 6,625,486 B2 | 9/2003 | Lundkvist et al. |
| 6,626,939 B1 | 9/2003 | Burnside et al. |
| 6,635,269 B1 | 10/2003 | Jennissen |
| 6,635,964 B2 | 10/2003 | Maex et al. |
| 6,645,135 B1 | 11/2003 | Bhat |
| 6,645,195 B1 | 11/2003 | Bhat et al. |
| 6,645,243 B2 | 11/2003 | Vallana et al. |
| 6,645,547 B1 | 11/2003 | Shekalim et al. |
| 6,656,162 B2 | 12/2003 | Santini, Jr. et al. |
| 6,656,216 B1 | 12/2003 | Hossainy et al. |
| 6,656,506 B1 | 12/2003 | Wu et al. |
| 6,660,034 B1 | 12/2003 | Mandrusov et al. |
| 6,663,662 B2 | 12/2003 | Pacetti et al. |
| 6,663,880 B1 | 12/2003 | Roorda et al. |
| 6,664,187 B1 | 12/2003 | Ngo et al. |
| 6,664,335 B2 | 12/2003 | Krishnan |
| 6,666,214 B2 | 12/2003 | Canham |
| 6,666,880 B1 | 12/2003 | Chiu et al. |
| 6,667,049 B2 | 12/2003 | Janas et al. |

| | | | | | |
|---|---|---|---|---|---|
| 6,669,723 B2 | 12/2003 | Killion et al. | 2002/0065553 A1 | 5/2002 | Weber |
| 6,669,980 B2 | 12/2003 | Hansen | 2002/0071822 A1 | 6/2002 | Uhrich |
| 6,673,105 B1 * | 1/2004 | Chen ............... 623/1.15 | 2002/0077693 A1 | 6/2002 | Barclay et al. |
| 6,673,154 B1 | 1/2004 | Pacetti et al. | 2002/0082679 A1 | 6/2002 | Sirhan et al. |
| 6,673,385 B1 | 1/2004 | Ding et al. | 2002/0082680 A1 * | 6/2002 | Shanley et al. ............. 623/1.16 |
| 6,676,697 B1 | 1/2004 | Richter | 2002/0087123 A1 | 7/2002 | Hossainy et al. |
| 6,676,700 B1 | 1/2004 | Jacobs et al. | 2002/0091433 A1 | 7/2002 | Ding et al. |
| 6,677,357 B2 * | 1/2004 | Zhu et al. ............. 514/326 | 2002/0094440 A1 | 7/2002 | Llanos et al. |
| 6,679,980 B1 | 1/2004 | Andreacchi | 2002/0111590 A1 | 8/2002 | Davila et al. |
| 6,689,099 B2 | 2/2004 | Mirzaee | 2002/0116050 A1 | 8/2002 | Kocur |
| 6,689,375 B1 | 2/2004 | Wahlig et al. | 2002/0120326 A1 | 8/2002 | Michal |
| 6,695,920 B1 | 2/2004 | Pacetti et al. | 2002/0138133 A1 | 9/2002 | Lenz et al. |
| 6,702,850 B1 * | 3/2004 | Byun et al. ............. 623/1.44 | 2002/0142039 A1 | 10/2002 | Claude |
| 6,703,307 B2 | 3/2004 | Lopatin et al. | 2002/0155212 A1 | 10/2002 | Hossainy |
| 6,706,013 B1 | 3/2004 | Bhat et al. | 2002/0161114 A1 | 10/2002 | Gunatillake et al. |
| 6,706,273 B1 | 3/2004 | Roessler | 2002/0165608 A1 | 11/2002 | Llanos et al. |
| 6,709,379 B1 | 3/2004 | Brandau et al. | 2002/0176849 A1 | 11/2002 | Slepian |
| 6,709,514 B1 | 3/2004 | Hossainy | 2002/0183581 A1 | 12/2002 | Yoe et al. |
| 6,712,845 B2 | 3/2004 | Hossainy | 2002/0187632 A1 | 12/2002 | Marsh |
| 6,713,119 B2 | 3/2004 | Hossainy et al. | 2002/0188037 A1 | 12/2002 | Chudzik et al. |
| 6,716,444 B1 | 4/2004 | Castro et al. | 2002/0188277 A1 | 12/2002 | Roorda et al. |
| 6,719,934 B2 | 4/2004 | Stinson | 2003/0003221 A1 | 1/2003 | Zhong et al. |
| 6,719,989 B1 | 4/2004 | Matsushima et al. | 2003/0004141 A1 | 1/2003 | Brown |
| 6,720,402 B2 | 4/2004 | Langer et al. | 2003/0028243 A1 | 2/2003 | Bates et al. |
| 6,723,120 B2 | 4/2004 | Yan | 2003/0028244 A1 | 2/2003 | Bates et al. |
| 6,733,768 B2 | 5/2004 | Hossainy et al. | 2003/0031780 A1 | 2/2003 | Chudzik et al. |
| 6,740,040 B1 | 5/2004 | Mandrusov et al. | 2003/0032767 A1 | 2/2003 | Tada et al. |
| 6,743,462 B1 | 6/2004 | Pacetti | 2003/0033001 A1 | 2/2003 | Igaki |
| 6,746,773 B2 | 6/2004 | Llanos et al. | 2003/0036794 A1 | 2/2003 | Ragheb et al. |
| 6,749,626 B1 | 6/2004 | Bhat et al. | 2003/0039689 A1 | 2/2003 | Chen et al. |
| 6,752,826 B2 | 6/2004 | Holloway et al. | 2003/0040712 A1 | 2/2003 | Ray et al. |
| 6,753,007 B2 | 6/2004 | Haggard et al. | 2003/0040790 A1 | 2/2003 | Furst |
| 6,753,071 B1 | 6/2004 | Pacetti et al. | 2003/0054090 A1 | 3/2003 | Hansen |
| 6,758,859 B1 | 7/2004 | Dang et al. | 2003/0055482 A1 | 3/2003 | Schwager et al. |
| 6,759,054 B2 | 7/2004 | Chen et al. | 2003/0059520 A1 | 3/2003 | Chen et al. |
| 6,764,505 B1 | 7/2004 | Hossainy et al. | 2003/0060877 A1 | 3/2003 | Falotico et al. |
| 6,774,278 B1 | 8/2004 | Ragheb et al. | 2003/0065377 A1 | 4/2003 | Davila et al. |
| 6,776,792 B1 | 8/2004 | Yan et al. | 2003/0072868 A1 | 4/2003 | Harish et al. |
| 6,783,793 B1 | 8/2004 | Hossainy et al. | 2003/0073961 A1 | 4/2003 | Happ |
| 6,818,063 B1 | 11/2004 | Kerrigan | 2003/0077310 A1 * | 4/2003 | Pathak et al. ............... 424/423 |
| 6,846,323 B2 | 1/2005 | Yip et al. | 2003/0083646 A1 | 5/2003 | Sirhan et al. |
| 6,849,089 B2 * | 2/2005 | Stoll ............... 623/1.42 | 2003/0083739 A1 | 5/2003 | Cafferata |
| 6,860,946 B2 | 3/2005 | Hossainy et al. | 2003/0088307 A1 | 5/2003 | Shulze et al. |
| 6,861,088 B2 | 3/2005 | Weber et al. | 2003/0093107 A1 | 5/2003 | Parsonage et al. |
| 6,865,810 B2 | 3/2005 | Stinson | 2003/0097088 A1 | 5/2003 | Pacetti |
| 6,869,443 B2 | 3/2005 | Buscemi et al. | 2003/0097173 A1 | 5/2003 | Dutta |
| 6,878,160 B2 | 4/2005 | Gilligan et al. | 2003/0099712 A1 | 5/2003 | Jayaraman |
| 6,887,270 B2 | 5/2005 | Miller et al. | 2003/0100865 A1 | 5/2003 | Santini, Jr. et al. |
| 6,887,485 B2 | 5/2005 | Fitzhugh et al. | 2003/0105518 A1 | 6/2003 | Dutta |
| 6,890,546 B2 | 5/2005 | Mollison et al. | 2003/0105530 A1 | 6/2003 | Pirhonen |
| 6,899,731 B2 | 5/2005 | Li et al. | 2003/0113439 A1 | 6/2003 | Pacetti et al. |
| 6,981,985 B2 * | 1/2006 | Brown et al. ............... 623/1.15 | 2003/0113445 A1 | 6/2003 | Martin |
| 2001/0007083 A1 | 7/2001 | Roorda | 2003/0138487 A1 | 7/2003 | Hogan et al. |
| 2001/0014717 A1 | 8/2001 | Hossainy et al. | 2003/0150380 A1 | 8/2003 | Yoe |
| 2001/0016753 A1 | 8/2001 | Caprio et al. | 2003/0157241 A1 | 8/2003 | Hossainy et al. |
| 2001/0020011 A1 | 9/2001 | Mathiowitz et al. | 2003/0158517 A1 | 8/2003 | Kokish |
| 2001/0029351 A1 | 10/2001 | Falotico et al. | 2003/0171053 A1 | 9/2003 | Sanders |
| 2001/0037145 A1 | 11/2001 | Guruwaiya et al. | 2003/0185964 A1 | 10/2003 | Weber et al. |
| 2001/0044652 A1 | 11/2001 | Moore | 2003/0187495 A1 | 10/2003 | Cully et al. |
| 2001/0051608 A1 | 12/2001 | Mathiowitz et al. | 2003/0190406 A1 | 10/2003 | Hossainy et al. |
| 2002/0002399 A1 | 1/2002 | Huxel et al. | 2003/0203617 A1 | 10/2003 | Lane et al. |
| 2002/0004060 A1 | 1/2002 | Heublein et al. | 2003/0207020 A1 | 11/2003 | Villareal |
| 2002/0004101 A1 | 1/2002 | Ding et al. | 2003/0208259 A1 | 11/2003 | Penhasi |
| 2002/0005206 A1 | 1/2002 | Falotico et al. | 2003/0209835 A1 | 11/2003 | Chun et al. |
| 2002/0007213 A1 | 1/2002 | Falotico et al. | 2003/0211230 A1 | 11/2003 | Pacetti et al. |
| 2002/0007214 A1 | 1/2002 | Falotico | 2003/0226833 A1 | 12/2003 | Shapovalov et al. |
| 2002/0007215 A1 | 1/2002 | Falotico et al. | 2003/0236565 A1 | 12/2003 | DiMatteo et al. |
| 2002/0009604 A1 | 1/2002 | Zamora et al. | 2004/0018296 A1 | 1/2004 | Castro et al. |
| 2002/0016625 A1 | 2/2002 | Falotico et al. | 2004/0029952 A1 | 2/2004 | Chen et al. |
| 2002/0032414 A1 | 3/2002 | Ragheb et al. | 2004/0047978 A1 | 3/2004 | Hossainy et al. |
| 2002/0032434 A1 | 3/2002 | Chudzik et al. | 2004/0047980 A1 | 3/2004 | Pacetti et al. |
| 2002/0051730 A1 | 5/2002 | Bodnar et al. | 2004/0052858 A1 | 3/2004 | Wu et al. |
| 2002/0062148 A1 | 5/2002 | Hart | 2004/0052859 A1 | 3/2004 | Wu et al. |

| | | | | | | |
|---|---|---|---|---|---|---|
| 2004/0054104 A1 | 3/2004 | Pacetti | | EP | 0 970 711 | 1/2000 |
| 2004/0060508 A1 | 4/2004 | Pacetti et al. | | EP | 0 972 498 | 1/2000 |
| 2004/0062853 A1 | 4/2004 | Pacetti et al. | | EP | 0 974 315 | 1/2000 |
| 2004/0063805 A1 | 4/2004 | Pacetti et al. | | EP | 0 982 041 | 3/2000 |
| 2004/0071861 A1 | 4/2004 | Mandrusov et al. | | EP | 1 023 879 | 8/2000 |
| 2004/0072922 A1 | 4/2004 | Hossainy et al. | | EP | 1 034 752 | 9/2000 |
| 2004/0073298 A1 | 4/2004 | Hossainy | | EP | 1 075 838 | 2/2001 |
| 2004/0086542 A1 | 5/2004 | Hossainy et al. | | EP | 1 103 234 | 5/2001 |
| 2004/0086550 A1 | 5/2004 | Roorda et al. | | EP | 1 192 957 | 4/2002 |
| 2004/0093077 A1 | 5/2004 | White et al. | | EP | 1 273 314 | 1/2003 |
| 2004/0096504 A1 | 5/2004 | Michal | | EP | 0 869 847 | 3/2003 |
| 2004/0098095 A1 | 5/2004 | Burnside et al. | | EP | 0 941 072 | 1/2004 |
| 2004/0098117 A1 | 5/2004 | Hossainy et al. | | FR | 2 753 907 | 4/1998 |
| 2004/0111149 A1 | 6/2004 | Stinson | | GB | 2 247 696 | 3/1992 |
| 2004/0127970 A1 | 7/2004 | Saunders | | GB | 2 316 086 | 1/2000 |
| 2004/0142015 A1 | 7/2004 | Hossainy et al. | | GB | 2 316 342 | 1/2000 |
| 2004/0143317 A1 | 7/2004 | Stinson et al. | | GB | 2 333 975 | 1/2000 |
| 2004/0167610 A1 | 8/2004 | Fleming, III | | GB | 2 336 551 | 1/2000 |
| 2004/0213893 A1 | 10/2004 | Boulais | | GB | 2 356 586 | 5/2001 |
| 2004/0236417 A1 | 11/2004 | Yan et al. | | GB | 2 356 587 | 5/2001 |
| 2005/0187607 A1* | 8/2005 | Akhtar et al. ............... 623/1.15 | | GB | 2 333 474 | 6/2001 |
| | | | | GB | 2 334 685 | 6/2001 |
| FOREIGN PATENT DOCUMENTS | | | | GB | 2 356 585 | 7/2001 |
| CA | 2 007 648 | 4/1991 | | GB | 2 374 302 | 8/2001 |
| CA | 1 322 628 | 10/1993 | | GB | 2 370 243 | 6/2002 |
| CA | 1 336 319 | 7/1995 | | GB | 2 384 199 | 7/2003 |
| CA | 1 338 303 | 5/1996 | | JP | 49-48336 | 12/1974 |
| DE | 042 24 401 | 1/1994 | | JP | 54-18310 | 7/1979 |
| DE | 044 07 079 | 9/1994 | | JP | 60-28504 | 7/1985 |
| DE | 197 31 021 | 1/1999 | | JP | 21199867 | 5/1994 |
| DE | 199 16 086 | 10/1999 | | JP | 8-33718 | 2/1996 |
| DE | 198 56 983 | 12/1999 | | JP | 10-151190 | 6/1998 |
| EP | 0 108 171 | 5/1984 | | JP | 2919971 B2 | 7/1999 |
| EP | 0 144 534 | 6/1985 | | JP | 2001-190687 | 7/2001 |
| EP | 0 301 856 | 2/1989 | | SU | 0872531 | 10/1981 |
| EP | 0 380 668 | 4/1989 | | SU | 0876663 | 10/1981 |
| EP | 0 351 314 | 1/1990 | | SU | 0905228 | 2/1982 |
| EP | 0 364 787 | 4/1990 | | SU | 0790725 | 2/1983 |
| EP | 0 396 429 | 11/1990 | | SU | 1016314 | 5/1983 |
| EP | 0 397 500 | 11/1990 | | SU | 0811750 | 9/1983 |
| EP | 0 464 755 | 1/1992 | | SU | 1293518 | 2/1987 |
| EP | 0 493 788 | 7/1992 | | SU | 1477423 | 5/1989 |
| EP | 0 526 606 | 9/1992 | | WO | WO 89/03232 | 4/1989 |
| EP | 0 514 406 | 11/1992 | | WO | WO 90/01969 | 3/1990 |
| EP | 0 517 075 | 12/1992 | | WO | WO 90/04982 | 5/1990 |
| EP | 0 540 290 | 5/1993 | | WO | WO 90/06094 | 6/1990 |
| EP | 0 553 960 | 8/1993 | | WO | WO 91/11176 | 8/1991 |
| EP | 0 554 082 | 8/1993 | | WO | WO 91/12846 | 9/1991 |
| EP | 0 565 251 | 10/1993 | | WO | WO 91/17744 | 11/1991 |
| EP | 0 578 998 | 1/1994 | | WO | WO 91/17789 | 11/1991 |
| EP | 0 604 022 | 6/1994 | | WO | WO 92/10218 | 6/1992 |
| EP | 0 621 017 | 10/1994 | | WO | WO 93/06792 | 4/1993 |
| EP | 0 623 354 | 11/1994 | | WO | WO 94/09760 | 5/1994 |
| EP | 0 627 226 | 12/1994 | | WO | WO 94/21196 | 9/1994 |
| EP | 0 649 637 | 4/1995 | | WO | WO 95/10989 | 4/1995 |
| EP | 0 665 023 | 8/1995 | | WO | WO 95/11817 | 5/1995 |
| EP | 0 701 802 | 3/1996 | | WO | WO 95/24929 | 9/1995 |
| EP | 0 701 803 | 3/1996 | | WO | WO 95/29647 | 11/1995 |
| EP | 0 709 068 | 5/1996 | | WO | WO 95/33422 | 12/1995 |
| EP | 0 716 836 | 6/1996 | | WO | WO 96/28115 | 9/1996 |
| EP | 0 732 087 | 9/1996 | | WO | WO 96/33672 | 10/1996 |
| EP | 0 832 618 | 9/1996 | | WO | WO 96/35516 | 11/1996 |
| EP | 0 756 853 | 2/1997 | | WO | WO 96/40174 | 12/1996 |
| EP | 0 809 999 | 12/1997 | | WO | WO 97/10011 | 3/1997 |
| EP | 0 832 655 | 4/1998 | | WO | WO 97/45105 | 12/1997 |
| EP | 0 834 293 | 4/1998 | | WO | WO 97/46590 | 12/1997 |
| EP | 0 850 604 | 7/1998 | | WO | WO 98/04415 | 2/1998 |
| EP | 0 850 651 | 7/1998 | | WO | WO 98/07390 | 2/1998 |
| EP | 0 879 595 | 11/1998 | | WO | WO 98/08463 | 3/1998 |
| EP | 0 910 584 | 4/1999 | | WO | WO 98/17331 | 4/1998 |
| EP | 0 923 953 | 6/1999 | | WO | WO 98/20863 | 5/1998 |
| EP | 0 953 320 | 11/1999 | | WO | WO 98/23228 | 6/1998 |
| | | | | WO | WO 98/32398 | 7/1998 |

| | | |
|---|---|---|
| WO | WO 98/36784 | 8/1998 |
| WO | WO 99/01118 | 1/1999 |
| WO | WO 99/03515 | 1/1999 |
| WO | WO 99/16386 | 4/1999 |
| WO | WO 99/38546 | 8/1999 |
| WO | WO 99/42147 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17459 | 3/2001 |
| WO | WO 01/17577 | 3/2001 |
| WO | WO 01/43727 | 6/2001 |
| WO | WO 01/45763 | 6/2001 |
| WO | WO 01/49338 | 7/2001 |
| WO | WO 01/51027 | 7/2001 |
| WO | WO 01/52772 | 7/2001 |
| WO | WO 01/57144 | 8/2001 |
| WO | WO 01/74414 | 10/2001 |
| WO | WO 01/91918 | 12/2001 |
| WO | WO 02/03890 | 1/2002 |
| WO | WO 02/26162 | 4/2002 |
| WO | WO 02/34311 | 5/2002 |
| WO | WO 02/47731 | 6/2002 |
| WO | WO 02/49771 | 6/2002 |
| WO | WO 02/056790 | 7/2002 |
| WO | WO 02/058753 | 8/2002 |
| WO | WO 02/087550 | 11/2002 |
| WO | WO 02/102283 | 12/2002 |
| WO | WO 03/000308 | 1/2003 |
| WO | WO 03/007918 | 1/2003 |
| WO | WO 03/007919 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/061841 | 7/2003 |
| WO | WO 03/072084 | 9/2003 |
| WO | WO 03/072086 | 9/2003 |
| WO | WO 03/080147 | 10/2003 |
| WO | WO 03/082368 | 10/2003 |
| WO | WO 03/099169 | 12/2003 |
| WO | WO 2004/000383 | 12/2003 |
| WO | WO 2004/009145 | 1/2004 |
| WO | WO 2004/017947 | 3/2004 |
| WO | WO 2004/017976 | 3/2004 |
| WO | WO 2004/023985 | 3/2004 |
| WO | WO 2004/024339 | 3/2004 |

OTHER PUBLICATIONS

U.S. Appl. No. 10/304,669, filed Nov. 25, 2002, Madriaga et al.
U.S. Appl. No. 10/317,435, filed Dec. 11, 2002, Hossainy et al.
U.S. Appl. No. 10/322,255, filed Dec. 17, 2002, Chen et al.
U.S. Appl. No. 10/409,410, filed Apr. 7, 2003, Pacetti.
U.S. Appl. No. 10/439,415, filed May 15, 2003, Perng.
U.S. Appl. No. 10/602,487, filed Jun. 23, 2003, Castro et al.
U.S. Appl. No. 10/630,250, filed Jul. 30, 2003, Pacetti et al.
U.S. Appl. No. 10/676,545, filed Sep. 30, 2003, Fox et al.
U.S. Appl. No. 10/680,905, filed Oct. 7, 2003, Pacetti et al.
U.S. Appl. No. 10/738,704, filed Dec. 16, 2003, Pacetti et al.
U.S. Appl. No. 10/741,214, filed Dec. 19, 2003, Pacetti.
U.S. Appl. No. 10/747,996, filed Dec. 29, 2003, Chen et al.
U.S. Appl. No. 10/750,139, filed Dec. 30, 2003, DesNoyer et al.
U.S. Appl. No. 10/805,036, filed Mar. 16, 2004, Pacetti.
U.S. Appl. No. 10/816,072, filed Mar. 31, 2004, Dugan et al.
U.S. Appl. No. 10/824,754, filed Apr. 15, 2004, Perng.
U.S. Appl. No. 10/833,902, filed Apr. 27, 2004, Chen et al.
U.S. Appl. No. 10/835,229, filed Apr. 28, 2004, Prabhu et al.
U.S. Appl. No. 10/835,656, filed Apr. 30, 2004, Hossainy et al.
U.S. Appl. No. 10/851,411, filed May 20, 2004, Chen.
U.S. Appl. No. 10/855,294, filed May 26, 2004, Pacetti et al.
U.S. Appl. No. 10/877,527, filed Jun. 24, 2004, Yan et al.
U.S. Appl. No. 10/897,244, filed Jul. 21, 2004, Hossainy et al.
U.S. Appl. No. 10/928,587, filed Aug. 26, 2004, Hossainy et al.
U.S. Appl. No. 10/931,853, filed Aug. 31, 2004, Hossainy et al.
U.S. Appl. No. 10/932,364, filed Aug. 31, 2004, Foreman et al.
Angioplasty.org., *Balloons and Stents*, http://www.ptca.org/devices04.html, printed Oct. 15, 2004, 2 pages.
Anonymous, *Bioabsorbable stent mounted on a catheter having optical coherence tomography capabilities*, Research Disclosure, pp. 1159-1162 (Sep. 2004).
Anonymous, *Capillary Action*, http://www.ndt-ed.org/EducationResources/CommunityCollege/PenetrantTest/Introduction/Keywords/pt1.htm, printed Aug. 12, 2005, 1 page.
Anonymous, *Capillary Force Lithography (CFL)*, Nano Processing and Organic Devices Lab, 2 pages (no date).
Anonymous, *Capillary Rise of Liquid in Different Vanes Under Variable Residual Acceleration*, http://www.zarm.uni-bremen.de/2forschung/grenzph/isoterm/cap_rise/kapst_en.htm, ZARM—University of Bremen, printed Jun. 25, 2003, 2 pages.
Anonymous, *Cardiologists Draw—Up The Dream Stent*, Clinica 710, pp. 15 (Jun. 17, 1996), http://www.dialogweb.com/cgi/document?reg=1061848202959, printed Aug. 25, 2003, 2 pages.
Anonymous, *Coating Techniques, Air Knife Coating*, http://www.ferron-magnetic.co.uk/coatings/airknife.htm, printed Jul. 1, 2003, 1 page.
Anonymous, *Coating Techniques, Gap Coating (Knife Over Roll, etc.)*, http://www.ferron-magnetic.co.uk/coatings/knife.htm, printed Jul. 1, 2003, 1 page.
Anonymous, *Coating Techniques, Gravure Coating*, http://www.ferron-magnetic.co.uk/coatings/gravure.htm, printed Jul. 1, 2003, 2 pages.
Anonymous, *Coating Techniques, Reverse Roll Coating*, http://www.ferron-magnetic.co.uk/coatings/revroll.htm, printed Jul. 1, 2003, 22 pages.
Anonymous, *Heparin-coated stents cut complications By 30%*, Clinica 732, pp. 17 (Nov. 18, 1996), http://www.dialogweb.com/cqi/document?reg=1061847871753, printed Aug. 25, 2003, 2 pages.
Anonymous, *Liquid Gravity Motor*, http://w_ww.drspark86.com/idea001.html, printed Jun. 24, 2003, 2 pages (no date).
Anonymous, *Porosimetry—Why characterize the porosity?* 42 pages (no date.).
Anonymous, *Rolling Therapeutic Agent Loading Device for Therapeutic Agent Delivery or Coated Stent* (Abstract 434009), Res. Disclos. pp. 974-975 (Jun. 2000).
Anonymous, *Stenting Continues to Dominate Cardiology*, http://www.dialogweb.com/cgi/document?reg=1061848017752, Clinica vol. 720, pp. 22 (Sep. 2, 1996), printed Aug. 25, 2003, 2 pages.
Anonymous, *Surface Energy (Surface Wetting Capability)*, http://www.ndt-ed.org/EducationResources/CommunityCollege/PenetrantTest/PTMaterials/surfaceenergy.htm, printed Apr. 6, 2004, 3 pages (no date).
Anonymous, *The 14$^{th}$ International Young Physicists Tournament, The winning report*, Research Center for Quantum Information, Slovak Academy of Sciences, 5 pages (no date).
Anonymous, *The Wicking Well System*, http://www.decorative.com/wicking.html, printed Jun. 24, 2003, 1 page.
Anonymous, *Typical Parylene Properties*, 3 pages (no date).
Anonymous, *Viscosity*, Commonwealth of Australia, 7 pages (no date).
Ansari, *End-to-End Tubal Anastomosis Using an Absorbable Stent*, Fertility and Sterility, vol. 32, No. 2, pp. 197-201 (Aug. 1979).
Ansari, *Tubal Reanastomosis Using Absorbable Stent*, International Journal of Fertility, vol. 23, No. 4, pp. 242-243 (1978).
Aoyagi et al., *Preparation of cross-linked aliphatic polyester and application to thermo-responsive material*, Journal of Controlled Release 32, pp. 87-96 (1994).
Barath et al., *Low Dose of Antitumor Agents Prevents Smooth Muscle Cell Proliferation After Endothelial Injury*, JACC vol. 3, No. 2, pp. 252A (Feb. 1989).

Barbucci et al., *Coating of commercially available materials with a new heparinizable Material*, Journal of Biomedical Materials Research, vol. 25, pp. 1259-1274 (1991).

Beach et al., *Xylylene Polymers*, Encyclopedia of Polymer Science and Engineering, vol. 17, 2nd Edition, pp. 990-1025 (1989).

Boston Scientific, *Express $^{2TM}$ Coronary Stent System*, http://www.bostonscientific.com/med_specialty/deviceDetail.jsp?task=tskBasicDevice.jsp&sectionId=4&relId=2,74,75,76&deviceId=11001&uniqueId=MPDB1180&clickType=endeca, printed Aug. 8, 2005, 1 page.

Bull, *Parylene Coating for Medical Applications*, Medical Product Manufacturing News, 2 pages (Mar. 1993).

Casper et al., *Fiber-Reinforced Absorbable Composite for Orthopedic Surgery*, Polymeric Materials Science and Engineering, vol. 53, pp. 497-501(1985).

Charlson et al., *Temperature Selective Deposition of Parylene-C*, IEEE Transactions of Biomedical Engineering, vol. 39, No. 2, pp. 202-206 (Feb. 1992).

Chen et al., *The Kinetics of Wicking of Liquid Droplets into Yarns*, submitted to the Textile Research Journal, pp. 1-30 (Apr. 2001).

Chung et al., *Inner core segment design for drug delivery control of thermo-responsive polymeric micelles*, Journal of Controlled Release, vol. 65, pp. 93-103 (2000).

Crowe et al., *Absorption and Intestinal Metabolism of SDZ-RAD and Rapamycin in Rats*, Drug Metabolism and Disposition, vol. 27, No. 5, pp. 627-632 (1999).

De Scheerder et al., *Biocompatibility of polymer-coated oversized metallic stents implanted in normal porcine coronary arteries*, Atherosclerosis, vol. 114, pp. 105-114 (1995).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9, No. 2, pp. 111-130 (Mar. /Apr. 1996).

Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9, No. 6, pp. 495-504 (Nov./Dec. 1996).

Detweiler et al., *Sutureless Anastomosis of the Small Intestine and the Colon in Pigs Using an Absorbable Intraluminal Stent and Fibrin Glue*, Journal of Investigative Surgery, vol. 8, No. 2, pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9, No. 1, pp. 13-26 (Jan./Feb. 1996).

Dev et al., *Kinetics of Drug Delivery to the Arterial Wall Via Polyurethane-Coated Removable Nitinol Stent: Comparative Study of Two Drugs*, Catheterization and Cardiovascular Diagnosis, vol. 34, pp. 272-278 (1995).

Devanathan et al., *Polymeric Conformal Coatings for Implantable Electronic Devices*, IEEE Transactions on Biomedical Engineering, vol. BME-27, No. 11, pp. 671-675 (1980).

Dichek et al., *Seeding of Intravascular Stents with Genetically Engineered Endothelial Cells*, Circulation, vol. 80, No. 5, pp. 1347-1353 (Nov. 1989).

Dreyer et al., *Critical Velocities in Open Capillary Flows*, pp. 604-609 (no date).

Duerig et al., *A comparison of balloon-and self-expanding stents*, Min. Invas. Ther. & Allied Technol., vol. 11, No. 4, pp. 173-178 (2002).

Dutkiewicz, *Some Advances in Nonwoven Structures for Absorbency, Comfort and Aesthetics*, AUTEX Research Journal, vol. 2, No. 3, pp. 153-165 (Sep. 2002).

EFD, *780S Series Spray Valves Valvemate™ 7040 Controller Operating Manual*, 24 pages (2002).

Eigler et al., *Local Arterial Wall Drug Delivery from a Polymer Coated Removable Metallic Stent: Kinetics, Distribution, and Bioactivity of Forskolin*, JACC, vol. 4A, pp. 701-701, Abstract (Feb. 1994).

Elbert et al., *Conjugate Addition Reactions Combined with Free-Radical Cross-Linking for the Design of Materials for Tissue Engineering*, Biomacromolecules, vol. 2, pp. 430-441 (2001).

Erickson et al., *Numerical Simulations of Capillary-Driven Flows in Nonuniform Cross-Sectional Capillaries*, Journal of Colloid and Interface Science, vol. 250, pp. 422-430 (2002).

Eskin et al., *Growth of Cultured Calf Aortic Smooth Muscle Cells on Cardiovascular Prosthetic Materials*, J. Biomed. Mater. Res. vol. 10, pp. 113-122 (1976).

Eskin et al., *Tissue Cultured Cells: Potential Blood Compatible Linings for Cardiovascular Prostheses*, Polymer Science and Technology, vol. 14, pp. 143-161 (no date).

Fischell et al., *Low-Dose, β-Particle Emission from 'Stent' Wire Results in Complete, Localized Inhibition of Smooth Muscle Cell Proliferation*, Circulation, vol. 90, No. 6, pp. 2956-2963 (Dec. 1994).

Fischell et al., *The Bx Velocity™ Stent*, 5 pages, Biocompatibles Ltd. (2001).

Gengenbach et al., *Evolution of the Surface Composition and Topography of Perflurinated Polymers Following Ammonia-Plasma Treatment*, Plasma Surface Modifications of Polymers, pp. 123-146 (1994).

Gercken et al., *Results of the Jostent Coronary Stent Graft Implantation in Various Clinical Settings: Procedural and Follow-Up Results*, vol. 56, No. 3, pp. 353-360 (2002).

Gölander et al., *RF-Plasma-Modified Polystyrene Surfaces for Studying Complement Activation*, J. Biomater. Sci. Plymer Edn., vol. 4, No. 1 pp. 25-30 (1992).

Guidant, *ACS RX Multi-Link™ Coronary Stent System*, 6 pages (no date).

Guidant, *Guidant Multi-Link Vision OTW Coronary Stent System*, 2 pages (no date).

Hahn et al., *Biocompatibility of Glow-Discharge-Polmerized Films and Vacuum-Deposited Parylene*, Journal of Applied Polymer Science: Applied Polymer Symposium 38, 55-64 (1984).

Hahn et al., *Glow Discharge Polymers as Coatings for Implanted Devices*, John M. Dalton Research Center, University of Missouri-Columbia and the Graduate Center for Materials Research, pp. 109-113 (1981).

He et al., *Assessment of Tissue Blood Flow Following Small Artery Welding with an Intraluminal Dissolvable Stent*, Microsurgery, vol. 19, No. 3, pp. 148-152 (1999).

Hehrlein et al., *Low-Dose Radioactive Endovascular Stents Prevent Smooth Muscle Cell Proliferation and Neointimal Hyperplasia in Rabbits*, Circulation, vol. 92, No. 6, pp. 1570-1575 (Sep. 15, 1995).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol., vol. 3, pp. 197-199 (1998).

Hollahan et al., *Attachment of Amino Groups to Polymer Surfaces by Radiofrequency Plasmas*, Journal of Applied Polymer Science, vol. 13, pp. 807-816 (1969).

Huang et al., *Biodegradable Polymers Derived from Aminoacids*, Macromol. Symp. 144, 7-32 (1999).

Impulse Jetting, *About Us*, http://www.impulsejetting.com/about.html, printed Dec. 18, 2000, 1 page.

Impulse Jetting, *Our Technology*, http://www.impulsejetting.com/tech1.html, printed Dec. 18, 2000, 1 page.

Inagaki et al., *Hydrophilic Surface Modification of Polyethylene by No-Plasma Treatment*, Adhesion Sci. Technol., vol. 4, No. 2, pp. 99-107 (1990).

Inoue et al., *An AB block copolymer of oligo(methyl methacrylate) and poly(acrylic acid) for micellar delivery of hydrophobic drugs*, Journal of Controlled Release, vol. 51, pp. 221-229 (1998).

International Search Report and Written Opinion of PCT Application No. PCT/US2004/026137 filed Aug. 11, 2004 (Jan. 31, 2005).

Itabashi et al., *Electroless Deposited CoWB for Copper Diffusion Barrier Metal*, International Interconnect Technology Conference, pp. 285-287 (2002).

John Ritchie Production Group, *Production of Stents* (presentation), 15 pages (Apr. 24, 2003).

Kataoka et al., *Block Copolymer Micelles as Vehicles for Drug Delivery*, Journal of Controlled Release vol. 24, pp. 119-132 (1993).

Katsarava et al., *Amino Acid-Based Bioanalogous Polymers. Synthesis and Study of Regular Poly(ester amide)s Based on Bis(α-amino acid)α,ω-*Alkylene Diesters, and Aliphatic Dicarbolic Acids*, Journal of Polymer Science, Part A: Polymer Chemistry, vol. 37, 391-407 (1999).

Kawai et al., *Physiologically Based Pharmacokinetics of Cyclosporine A: Extension to Tissue Distribution Kinetics in Rats and Scale-up to Human*, The Journal of Pharmacology and Experimental Therapeutics, vol. 287, No. 2, pp. 457-468 (1998).

Kelley et al., *Totally Resorbable High-Strength Composite Material*, Advances in Biomedical Polymers, vol. 35, pp. 75-85 (1987).

Klocke et al, *How Soil Holds Water* (G90-964), http://ianrpubs.unl.edu/fieldcrops/g964.htm, printed Apr. 6, 2004, 9 pages.

Konopka, *In-Plane Moisture Transport in Nonwovens*, Nonwovens Cooperative Research Center, NC State University, 56 pages.

Kovarik et al., *Pharmacokinetic and Pharmacodynamic Assessments of HMG-CoA Reductase Inhibitors When Coadministered with Everolimus*, Journal of Clinical Pharmacology, vol. 42, pp. 222-228 (2002).

Kubies et al., *Microdomain Structure In polylactide-block-poly(ethylene oxide) copolymer films*, Biomaterials, vol. 21, pp. 529-536 (2000).

Kutryk et al., *Coronary Stenting: Current Perspectives, a companion to the Handbook of Coronary Stents*, 16 pages (1999).

Lambert et al., *Localized Arterial Wall Drug Delivery From a Polymer-Coated Removable Metallic Stent*, Circulation, vol. 90, No. 2, pp. 1003-1011 (Aug. 1994).

Lemos et al., *Coronary Restenosis After Sirolimus-Eluting Stent Implantation*, Circulation, vol. 108, No. 3, pp. 257-260 (Jul. 22, 2003).

Levy et al., *Strategies For Treating Arterial Restenosis Using Polymeric Controlled Release Implants*, Biotechnology and Bioactive Polymers, pp. 259-268 (1994).

Liermann et al., *Prophylactic Endovascular Radiotherapy to Prevent Intimal Hyperplasia after Stent Implantation in Femoropopliteal Arteries*, CardioVascular and Interventional Radiology, vol. 17, pp. 12-16 (1994).

Liu et al., *Drug Release Characteristics of Unimolecular Polymeric Micelles*, Journal of Controlled Release, vol. 68, pp. 167-174 (2000).

Loeb et al., *Parylene as a Chronically Stable, Reproducible Microelectrode Insulator*, IEEE Transactions on Biomedical Engineering, Mar. 1977 (pp. 121-128).

Loh et al., *Plasma Enhanced Parylene Deposition*, Antec, pp. 1099-1103, 1991.

Machine Solutions, *FFS700 MSI Balloon Form/Fold/Set Equipment (PTCA), FFS800 MSI Balloon Form/Fold/Set Equipment (PTA)*, http://machinesolutions.org/ffs7_8.html, printed Nov. 21, 2003 (2 pgs.).

Machine Solutions, *SC700 MSI Stent Crimping Equipment (PTCA), SC800 MSI Stent Crimping Equipment (PTA)*, http://www.machinesolutions.org/sc7_8.html, printed Nov. 21, 2003, 2 pages.

Malik et al., *Development of an Energetic Ion Assisted Mixing and Deposition Process for $TIN_x$ and Diamondlike Carbon Films, Using a Co-axial Geometry in Plasma Source Ion Implantation*, J. Vac. Sci. Technol. A, vol. 15, No. 6 pp. 2875-2879 (Nov./Dec. 1997).

Malik et al., *Overview of plasma source ion implantation research at University of Wisconsin-Madison*, J. Vac. Sci. Technol. B, No. 12, vol. 2, pp. 843-849 (Mar./Apr. 1994).

Malik et al., *Sheath dynamics and dose analysis for planar targets in plasma source ion implantation*, Plasma Sources Sci. Technol. vol. 2, pp. 81-85 (1993).

Marconi et al., *Covalent bonding of heparin to a vinyl copolymer for biomedical applications*, Biomaterials, vol. 18, No. 12, pp. 885-890 (1997).

Martin et al., *Enhancing the biological activity of immobilized osteopontin using a type-1 collagen affinity coating*, J. Biomed. Mater. Res., vol. 70A, pp. 10-19 (2004).

Matsumaru et al., *Embolic Materials For Endovascular Treatment of Cerebral Lesions*, J. Biomater. Sci. Polymer Edn., vol. 8, No. 7, pp. 555-569 (1997).

Mauduit et al., *Hydrolytic degradation of films prepared from blends of high and low molecular weight poly(DL-lactic acid)s*, J. Biomed. Mater. Res., vol. 30, pp. 201-207 (1996).

Middleton et al., *Synthetic biodegradable polymers as orthopedic devices*, Biomaterials, vol. 21, pp. 2335-2346 (2000).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull., vol. 33, No. 6, pp. 2490-2498 (1985).

Miyazawa et al., *Effects of Pemirolast and Tranilast on Intimal Thickening After Arterial Injury in the Rat*, J. Cardiovasc. Pharmacol., vol. 30, No. 2, pp. 157-162 (1997).

Moody, *Vacuum Coating Ultrasonic Transducers*, 1 page, Sensors (Dec. 1993).

Muller et al., *Advances in Coronary Angioplasty: Endovascular Stents*, Coronary Artery Disease, vol. 1, No. 4., pp. 438-448 (Jul./Aug. 1990).

Neimark et al., *Hierarchical Pore Structure and Wetting Properties of Single-Wall Carbon Nanotube Fibers*, Nano Letters, vol. 3, No. 3, pp. 419-423 (2003).

Nichols et al., *Electrical Insulation of Implantable Devices by Composite Polymer Coatings*; ISA Transactions, vol. 26, No. 4, pp. 15-18 (1987).

Nordrehaug et al., *A Novel Biocompatible Coating Applied to Coronary Stents*, EPO Heart Journal 14, p. 321 (P1694), Abstr. Suppl. (1993).

Nova Tran™ Custom Coating Services, *Parylene Conformal Coating*, 8 pages (no date).

Ohsawa et al., *Preventive Effects of an Antiallergic Drug, Pemirolast Potassium, on Restenosis After Percutaneous Transluminal Coronary Angioplasty*, American Heart Journal, vol. 136, No. 6, pp. 1081-1087 (Dec. 1998).

Olson, *Parylene, a Biostabel Coating for Medical Applications*, Specialty Coating Systems, Inc. Nova Tran™ Parylene Coating Services (no date).

Ozaki et al., *New Stent Technologies*, Progress in Cardiovascular Diseases, vol. XXXIX, No. 2, pp. 129-140 (Sep./Oct. 1996).

Para Tech Coating Company, *Galxyl, Parylene Coatings by Para Tech*, 1 page (no date).

Para Tech Coating Company, *Lab Top® Parylene Deposition System*, 2 pages (no date).

Pechar et al., *Poly(ethylene glycol) Multiblock Copolymer as a Carrier of Anti-Cancer Drug Doxorubicin*, Bioconjucate Chemistry vol. 11, No. 2, pp. 131-139 (Mar./ Apr. 2000).

Peng et al., *Role of polymers in improving the results of stenting in coronary arteries*, Biomaterial, vol. 17, pp. 685-694 (1996).

Peuster et al., *A novel approach to temporary stenting: degradable cardiovascular stents produced from corrodible metal-results 6-18 months after implantation into New Zealand white rabbits*, Heart vol. 86, pp. 563-569 (2001).

Pietrzak et al., *Bioabsorbable Fixation Devices: Status for the Craniomaxillofacial Surgeon*, Journal of Craniofacial Surgery, vol. 8, No. 2, pp. 92-96 (1997).

Pietrzak et al., *Bioresorbable Implants—Practical Considerations*, Bone, vol. 19, No. 1, Supplement, pp. 109S-119S (Jul. 1996).

Poncin-Epaillard et al., *Reactivity of a Polypropylene Surface Modified in a Nitrogen Plasma*, Plasma Surface Modification of Polymers pp. 167-180 (1994).

Prabhu, *Computational Modeling in Stent-based Drug Delivery*, Business Briefing: Medical Device Manufacturing & Technology, 4 pages (2004).

Redman, *Clinical Experience with Vasovasostomy Utilizing Absorbable Intravasal Stent*, Urology, vol. XX, No. 11, pp. 59-61 (Jul. 1982).

Refracton Techonolgies, Corp., *Fine Bubble Diffusers*, 2 pages (do date).

Refracton Techonolgies, Corp., *Refractron Advanced Porous Ceramic Product Capabilities*, http://www.refractron.com/ecom/sp/cat=Product+Information, printed Apr. 6, 2004, 3 pages.

Refractron Technologies Corp., http://www.refractron.com/ecom/sp/cat=Custom+Applications, printed Jun. 24, 2003, 1 page.

Rust et al., *The Effect of Absorbable Stenting on Postoperative Stenosis of the Surgically Enlarged Maxillary Sinus Ostia in a Rabbit Animal Model*, Archives of Otolaryngology, Head and Neck Surgery, vol. 122, pp. 1395-1397 (Dec. 1996).

Sadhir et al., *The Adhesion of Glow-Discharge Polymers, Silastic And Parylene to Implantable Platinum Electrodes: Results of Tensil Pull tests After Exposure to Isotonic Sodium Chloride*, Biomaterials, vol. 2, pp. 239-243 (Oct. 1981).

Saotome, et al., *Novel Enzymatically Degradable Polymers Comprising α-Amino Acid, 1,2-Ethanediol, and Adipic Acid*, Chemistry Letters, pp. 21-24, (1991).

Schatz, *A View of Vascular Stents*, Circulation, vol. 79, No. 2, pp. 445-457 (Feb. 1989).

Scheuer et al., *Model of plasma source ion implantation in planar, cylindrical, and spherical geometries*, J. Appl. Phys., vol. 67, No. 3, pp. 1241-1245 (Feb. 1990).

Schmidt et al., *Long-term Implants of Parylene-C Coated Microelectrodes*, Medical & Biological Engineering & Computing, pp. 96-101 (Jan. 1988).

Serkova et al., *Tissue Distribution and Clinical Monitoring of the Novel Macrolide Immunosuppressant SDZ-RAD and its Metabolites in Monkey Lung Transplant Recipients: Interaction with Cyclosporine*, The Journal of Pharmacology and Experimental Therapeutics, vol. 294, No. 1, pp. 323-332 (2000).

Serruys et al., *I Like the Candy, I Hate the Wrapper; the $^{32}P$ Radioactive Stent*, Circulation, vol. 101, pp. 3-7 (Jan. 2000).

Shamim et al., *Measurement of electron emission due to energetic ion bombardment in plasma source ion implantation*, J. Appl. Phys., vol. 70, No. 9, pp. 4756-4759 (Nov. 1991).

Shamim et al., *Measurements of Spatial and Temporal Sheath Evolution for Spherical and Cylindrical Geometries in Plasma Source Ion Implantation*, J. Appl. Phys., vol. 69, No. 5, pp. 2904-2908 (Mar. 1991).

Shigeno, *Prevention of Cerebrovascular Spasm By Bosentan, Novel Endothelin Receptor*, Chemical Abstract 125:21230 (1996).

Sono Tek Corporation, *AccuMist™ for Single Stent Coating Applications*, http://www.sono-tek.com/biomedical/accumist_stent.html, printed Aug. 2, 2005, 3 pages.

Sono Tek Corporation, *MediCoat™ DES 1000, Benchtop Stent Coating System*, http://www.sono-tek.com/biomedical/medicoat_standalone.html, printed Aug. 2, 2005, 4 pages.

Sono Tek Corporation, *MicroMist for Stent Coating*, http://www.sono-tek.com/biomedical/micromist_stent.html, printed Aug. 2, 2005, 3 pages.

Spagnuolo et al., *Gas 1 is induced by VE-cadherin and vascular endothelial growth factor and inhibits endothelial cell apoptosis*, Blood, vol. 103, No. 6, pp. 3005-3012 (2004).

Specialty Coating Systems, Inc., *The Parylene Press*, 4 pages (Summer 1993).

Specialty Coating Systems, Inc., *The Parylane Press*, 6 pages (Spring 1993).

Specialty Coating Systems, Inc., *The Parylene Press*, 7 pages (Winter 1992).

Specialty Coating Systems, *Parylene and Nova Tran™ Parylene Coating Services, for Unmatched Conformal Coating Performance*, 21 pages (no date).

Specialty Coating Systems, *Parylene, a Biostable Coating for Medical Applications*, 6 pages (no date).

Specialty Coating Systems, *Repair and Recoating of Parylene Coated Printed Circuit Boards*, 15 pages (no date).

Straube, *Moisture, Materials, & Buildings*, HPAC Engineering, pp. 2-7 (no date).

Taher, *Capillary interaction between a small thin solid plate and a liquid*, Mechanical and Industrial Engineering, University of Illinois at Urbana-Champaign, 4 pages (undated).

Tamai et al., *Initial and 6-Month Results of Biodegradable Poly-I-Lactic Acid Coronary Stents in Humans*, Circulation, vol. 102, pp. 399-404 (2000).

Trident, Inc., http://www.tridentintl.com/subbody.html, printed Dec. 18, 2000, 1 page.

Trident, Inc., *Product Lines*, http://www.tridentintl.com/products-apps/ultrajet.html, printed Dec. 18, 2000, 3 pages.

Tsuji et al., *Biodegradable Polymeric Stents*, Current Interventional Cardiology Reports vol. 3, pp. 10-17 (2001).

Union Carbide Adhesion Promoters, *Union Carbide A-174 Silane*, 5 pages (Jan. 1968).

Union Carbide Electronics Division, *Parylene Environmentally Compatible Conformal Coatings for Electronic Components Assemblies and Precision Parts*, 14 pages (no date).

Union Carbide, *Abrasion Resistance of Parylene and Other Conformal Circuit Board Coatings*, Parylene Products, No. 4, 13 pages (Oct. 1977).

Union Carbide, *Adhesion Promotion Systems for Parylene*, Parylene Products, No. 15, Revision 1, 8 pages (Oct. 1977).

Union Carbide, *Adhesion Promotion Systems for Parylene*, Technology Letter, No. 15, 13 pages (Oct. 1975).

Union Carbide, *Evaluation of Parylene and Other Pellicles as Beam Splitters*, Parylene Products, No. 8, Edited, 19 pages (Oct. 1977).

Union Carbide, *Fluorescent Parylene Coatings*, Parylene Products, No. 7 Revision 1, 8 pages (Oct. 1977).

Union Carbide, *Fluorescent Parylene Coatings*, Technology Letter, No. 7, 8 pages (Oct. 1973).

Union Carbide, *Mechanical Protection Criteria for Thin Conformal Coatings*, Parylene Products, No. 3, 21 pages (Oct. 1977).

Union Carbide, *Method for Repair and Patching of Parylene Coated Printed Circuit Boards*, Parylene Products, No. 2 Revision 1, 9 pages (Oct. 1977).

Union Carbide, *Microencapsulation by Vapor Deposition*, Parylene Products, No. 6, 12 pages (Oct. 1977).

Union Carbide, *MIL I 46058, Qualification of Patylene N, C, and D*, Parylene Products, No. 1 Revision 2, 8 pages (Oct. 1977).

Union Carbide, *Parylene Bibliography*, Parylene Products, No. 5, Revision 4, 17 pages (Jan. 18, 1982).

Union Carbide, *Parylene Conformal Coatings for Hybrid Microelectronics*, Parylene Products, No. 9, 23 pages (Oct. 1973).

Union Carbide, *Parylene Pellicles for Space Applications*, Parylene Products, No. 10, 50 pages (Oct. 1977).

Union Carbide, *Parylene Pyrolysis Kinetics*, Parylene Products, No. 11, 12 pages (Oct. 1977).

Union Carbide, *Parylene Pyrolysis Kinetics*, Technology Letter, No. 11, 12 pages (May 1974).

Union Carbide, *Parylene Removal with Oxygen Plasmas*, Parylene Products, No. 18, 7 pages (Aug. 1977).

Union Carbide, *Printed Circuit Board Masking Techniques for Use with Parylene*, No. 14, Revision 1, 11 pages (Oct. 1977).

Union Carbide, *Solvent Resistance of the Parylenes*, Parylene Products, No. 12, Revision 1, 5 pages (Oct. 1977).

Union Carbide, *The Selective Removal of Parylene by Plasma Etching*, No. 13, Revision 1, 7 pages (Oct. 1977).

Union Carbide, *Thermal Endurance of the Parylenes in Air*, Parylene Products, No. 16, 4 pages (Mar. 1976).

Union Carbide, *Vapor Phase Adhesion Promotion Systems*, Parylene Products, No. 17, Revision 1, 11 pages (Oct. 1977).

van Beusekom et al., *Coronary Stent Coatings*, Coronary Artery Disease, vol. 5, No. 7, pp. 590-596 (Jul. 1994).

van der Giessen et al., *"Edge Effect " of $^{32}P$ Radioactive Stents is Caused by the Combination of Chronic Stent Injury and Radioactive Dose Falloff*, Circulation, vol. 104, pp. 2236-2241 (Oct. 30, 2001).

Vapor Inc., *Vapore-Jet™ Capillary Pump—How it Works*, http://www.vapore.com/tech_howto.htm, printed Aug. 13, 2003, 2 pages.

Völkel et al., *Targeting of immunoliposomes to endothelial cells using a single -chain Fv fragment directed against human endoglin (CD105)*, Biochemica et Biophysica Acta, vol. 1663, pp. 158-166 (2004).

von Recum et al., *Degradation of polydispersed poly(L-lactic acid) to modulate lactic acid release*, Biomaterials, vol. 16, pp. 441-445 (1995).

Wiesendanger et al., *Contributions of Scanning Probe Microscopy and Spectroscopy to the Investigation and Fabrication of Nanometer-Scale Structures*, J. Vac. Sci. Technol. B, vol. 12, No. 2, pp. 515-529 (Mar./Apr. 1994).

Wilensky et al., *Methods and Devices for Local Drug Delivery in Coronary and Peripheral Arteries*, Trends Cardiovasc. Med., vol. 3, No. 5, pp. 163-170 (1993).

Wong et al., *An Update on Coronary Stents*, Cardio, 8 pages (Feb. 1992).

World Precision Instruments, Inc., http://www.wpiinc.com/WPI_Web/Pumps/pneumatic_Fig.gif, printed Sep. 30, 2002, 1 page.

World Precision Instruments, Inc., *Nanoliter Injector*, http://www.wpiinc.com/WPI_Web/Microinjection/Nanoliter_Injector.html, printed Jun. 10, 2005, 3 pages.

World Precision Instruments, Inc., *Nanoliter Injector*, http://www.wpi-europe.com/products/microinjection/nanoliter.htm printed Jun. 10, 2005, 2 pages.

World Precision Instruments, Inc., *Pneumatic PicoPumps*, http://www.wpieurope.com/products/microinjection/picopumps.htm, printed Jun. 10, 2005, 4 pages.

World Precision Instruments, Inc., *Pneumatic PicoPumps*, http://www.wpiinc.com/WPI_Web/Microinjection/Pneumatic_PicoPumps.html, printed Jun. 10, 2005, 4 pages.

Yau et al., *Modern Size-Exclusion Liquid Chromatography*, Wiley-Interscience Publication, 9 pages (1979).

Yokoyama et al., *Characterization of physical entrapment and chemical conjugation of adriamycin in polymeric micelles and their design for in vivo delivery to asolid tumor*, Journal of Controlled Release, vol. 50, pp. 79-92 (1998).

Yuen et al., *Tissue response to potential neuroprosthetic materials implanted subdurally*, Biomaterials, vol. 8, pp. 57-62 (Mar. 1987).

Zhmud et al., *Dynamics of Capillary Rise*, Journal of Colloid and Interface Science, vol. 228, pp. 263-269 (2000).

Zimarino et al., *Analysis of Stent Edge Restenosis with Different Forms of Brachytherapy*, The American Journal of Cardiology, vol. 89, pp. 322-325 (Feb. 1, 2002).

Zylberman et al., *Comparative Study of Electroless Co(W,P) and Co(Mo,P) Thin-Films for Capping and Barrier Layers for Cu Metallization*, 2002 Advanced Metallization Conference, 2 pages (no date).

European Search Report for application 05853635.0-2107, mailed Jan. 21, 2008, 3 pgs.

* cited by examiner

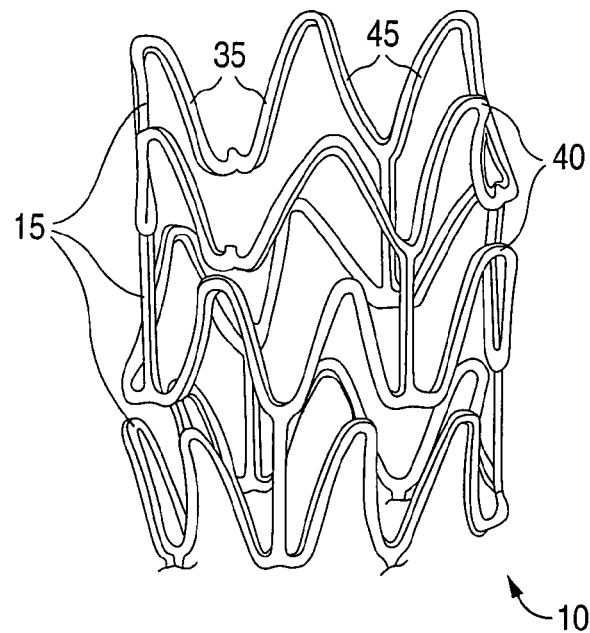
FIG. 1
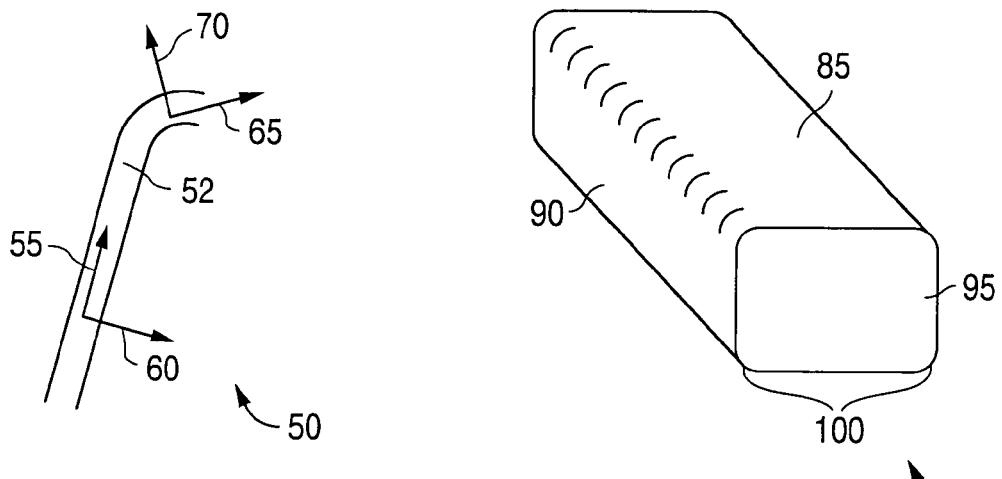
FIG. 2
FIG. 3
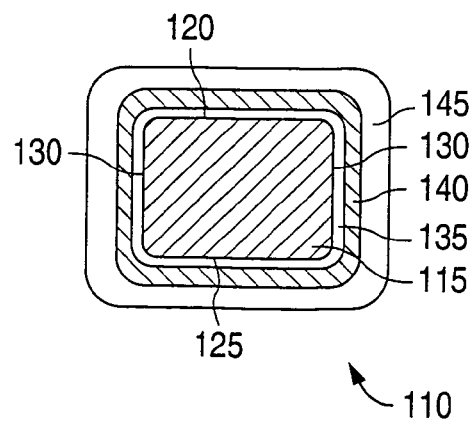
FIG. 4

ABLUMINAL, MULTILAYER COATING CONSTRUCTS FOR DRUG-DELIVERY STENTS

BACKGROUND OF THE INVENTION

1. Field of the Invention

The invention relates to drug delivery implantable medical devices, one example of which is a stent. More particularly, the invention relates to abluminal, multilayer coating constructs for drug-delivery stents.

2. Description of the Background

This invention relates to radially expandable endoprostheses, which are adapted to be implanted in a bodily lumen. An "endoprosthesis" corresponds to an artificial implantable medical device that is placed inside the body. A "lumen" refers to a cavity of a tubular organ such as a blood vessel. A stent is an example of these endoprostheses. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expansion of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen. In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn which allows the stent to self-expand.

Stents have been made of many materials including metals and polymers. Polymeric materials include both nonbioerodable and bioerodable plastic materials. The cylindrical structure of stents is typically composed of a scaffolding that includes a pattern or network of interconnecting structural elements or struts. The scaffolding can be formed from wires, bars, tubes, or planar films of material rolled into a cylindrical shape. Furthermore, the pattern that makes up the stent allows the stent to be radially expandable and longitudinally flexible. Longitudinal flexibility facilitates delivery of the stent, and rigidity is needed to hold open a body lumen. The pattern should be designed to maintain the longitudinal flexibility and rigidity required of the stent.

Stents are used not only for mechanical intervention but also as vehicles for providing biological therapy. Biological therapy can be achieved by medicating the stents. Medicated stents provide for the local administration of a therapeutic substance at the diseased site. In order to provide an efficacious concentration to the treated site, systemic administration of such medication often produces adverse or even toxic side effects for the patient. Local delivery is a preferred method of treatment in that smaller total levels of medication are administered in comparison to systemic dosages, but are concentrated at a specific site. Local delivery thus produces fewer side effects and achieves more favorable results.

A medicated stent may be fabricated by coating the surface of either a metallic or polymeric scaffolding to produce a drug reservoir layer on the surface. The drug reservoir layer typically includes a polymeric carrier that includes an active agent or drug. To fabricate a coating, a polymer, or a blend of polymers, can be applied on the stent using commonly used techniques known to those having ordinary skill in the art. A composition for application to a stent may include a solvent, a polymer dissolved in the solvent, and an active agent dispersed in the blend. The composition may be applied to the stent by immersing the stent in the composition, by direct application, by roll coating, or by spraying the composition onto the stent. The solvent is allowed to evaporate, leaving on the stent strut surfaces a coating of the polymer and the active agent impregnated in the polymer.

A drug delivery stent coating should meet several well-known criteria including mechanical integrity, controlled release of the drug, and biocompatibility. Active agents within polymer-based coating layers can interfere with the mechanical integrity of a coating since active agents negatively impact the coating mechanical properties, and the ability of a polymer matrix to adhere effectively to the surface of the stent. Increasing the quantity of the active agent reduces the effectiveness of the adhesion. A primer layer can serve as a functionally useful intermediary layer between the surface of the device and an active agent-containing or reservoir coating, or between multiple layers of reservoir coatings. The primer layer provides an adhesive tie between the reservoir coating and the device. In addition, successful treatment of a diseased site with a medicated stent often requires that the rate of release of the active agent or drug be within a prescribed range. A barrier or polymeric topcoat layer above a reservoir layer serves the purpose of controlling the rate of release of an active agent or drug.

Furthermore, since the presence of foreign polymers can adversely affect the body, it is generally desirable to limit exposure of the polymer on a coating to the body. Therefore, a stent may also include a biobeneficial coating over a reservoir layer and/or topcoat layer to improve the biocompatibility of the coating. However, in general, it is appropriate to use no more polymer than is necessary to hold the drug on the stent and to control its release. This is particularly the case for coatings that include bioabsorbable polymers since the polymer is absorbed in vivo. Therefore, it would be advantageous to reduce the amount of coating material on a stent without adversely impacting the stent's treatment capabilities.

Additionally, the presence of a topcoat layer, such as a poly(ester amide) (PEA) layer, on a luminal stent surface can have a detrimental impact on a stent's deliverability and coating mechanical integrity. The PEA coatings change the coefficient of friction between the stent and the delivery balloon. In addition, some PEA polymers have structures that cause them to be sticky or tacky. If the PEA either increases the coefficient of friction or adheres to the catheter balloon, the smooth release of the stent from the balloon after deflation is compromised. PEA stent coatings often exhibit extensive balloon shear damage post-deployment as well, which could result in a thrombogenic luminal stent surface. Therefore, it would be desirable to limit exposure of the balloon to the PEA topcoat layer.

SUMMARY

Embodiments of the present invention are directed to coatings for implantable medical devices, such as stents. The devices may include a structural element having a surface with an abluminal side, a luminal side, and two sidewalls extending between the abluminal side and the luminal side. The coating may include a continuous first layer disposed above all or a majority of the abluminal side and optionally above a portion of at least one of the side-walls extending from the abluminal side. The luminal side and portions of the sidewalls are free from the first layer. The coating may further include a continuous second layer covering the first layer such that no portion of the first layer is not covered by the second layer. The luminal side of the structural element is free from the second layer.

A further embodiment of the invention may a include a coating for the structural element including a continuous first layer disposed above all or a majority of the abluminal side and optionally above a portion of at least one of the side-walls extending from the abluminal side. The luminal side and portions of the sidewalls are free from the first layer. The coating may further include a continuous second layer covering a portion of the first layer such that at least a portion of the first layer is not covered by the second layer.

BRIEF DESCRIPTION OF THE FIGURES

FIG. 1 depicts a stent.

FIG. 2 depicts a planar projection of a portion of a stent.

FIG. 3 depicts a portion of a structural element of a stent.

FIG. 4 depicts a cross-section of a structural element of a stent with a coating.

DETAILED DESCRIPTION

Figure 5:
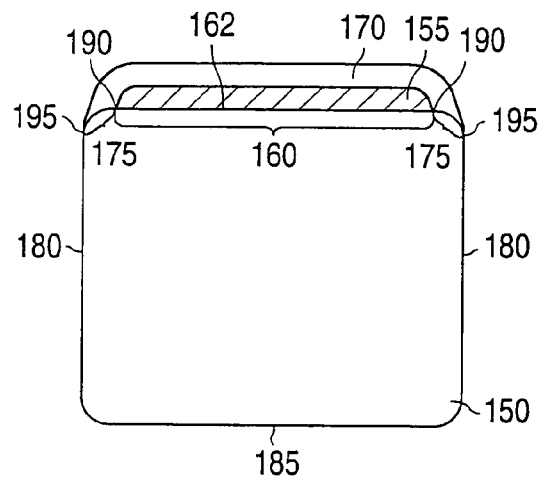
FIG. 5 depicts a cross-sectional view of an embodiment of an abluminally coated structural element of a stent.

Embodiments of the invention described herein relate to drug delivery implantable medical devices. In particular, various embodiments of devices with abluminal, multilayer coating constructs for drug-delivery are described. The embodiments of devices described herein relate to implantable medical devices that include an underlying scaffolding or substrate with a coating such as a polymer-based coating. The polymer-based coating may contain, for example, an active agent or drug for local administration at a diseased site. The active agent can be any substance capable of exerting a therapeutic or prophylactic effect. The underlying substrate that is coated can be polymeric, metallic, ceramic, or made from any suitable material. "Implantable medical device" is intended to include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure or substrate of the device can be of virtually any design.

The underlying structure or substrate of an implantable medical device, such as a stent can be completely or at least in part be made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

To fabricate the coating, the polymer, or a blend of polymers, can be applied on the stent using commonly used techniques known to those having ordinary skill in the art. For example, the polymer can be applied to the stent by dissolving the polymer in a coating solvent, or a mixture of solvents, and applying the resulting solution on the stent by spraying, "ink-jet-type" deposition methods, brushing, roll coating, plasma deposition, and the like. "Solvent" is defined as a substance capable of dissolving or dispersing one or more other substances or capable of at least partially dissolving or dispersing the substance(s) to form a uniformly dispersed mixture at the molecular- or ionic-size level. The solvent should be capable of dissolving at least 0.1 mg of the polymer in 1 ml of the solvent, and more narrowly 0.5 mg in 1 ml at ambient temperature and ambient pressure.

Polymers can be biostable, bioabsorbable, biodegradable, or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and eventual absorption and elimination of the polymer can be caused by, for example, hydrolysis, metabolic processes, bulk or surface erosion, and the like. For coating applications, it is understood that after the process of degradation, erosion, absorption, and/or resorption has been completed, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug delivery is accomplished.

Representative examples of polymers that may be used in the embodiments of the substrate of implantable medical devices or coatings for implantable medical devices disclosed herein include, but are not limited to, poly(N-acetylglucosamine) (Chitin), Chitosan, poly(hydroxyvalerate), poly (lactide-co-glycolide), poly(hydroxybutyrate), poly(hydroxybutyrate-co-valerate), polyorthoester, polyanhydride, poly(glycolic acid), poly(glycolide), poly(L-lactic acid), poly (L-lactide), poly(D,L-lactic acid), poly(D,L-lactide), poly (D-lactic acid), poly(D-lactide), poly(D,L-lactide-co-L-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene fluoride and polyvinylidene chloride), polyacrylonitrile, polyvinyl ketones, polyvinyl aromatics (such as polystyrene), polyvinyl esters (such as polyvinyl acetate), poly(methacrylates), poly(acrylates), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in embodiments of the substrate of implantable medical devices or coatings for implantable medical devices disclosed herein include ethylene vinyl alcohol copolymer (commonly known by the generic name EVOH or by the trade name EVAL), poly(butyl methacrylate), poly(vinylidene fluoride-co-hexafluoropropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

In addition, polymers containing moieties derived from poly(lactic acid) can be also used in addition to or instead of, poly(lactic acid), for fabricating and coating devices. Polymers based on poly(lactic acid) include derivatives of poly (lactic acid), for example, hydrolyzed or carboxylated poly (lactic acid), or a blend thereof. Using hydrolyzed or carboxylated poly(lactic acid) is expected to result in an increased rate of degradation of the coating. Another type of polymer based on poly(lactic acid) that can be used for fabricating and coating implantable medical devices includes graft copolymers, and block copolymers, such as AB block-copolymers ("diblock-copolymers") or ABA block-copolymers ("triblock-copolymers"), or mixtures thereof.

Examples of active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The bioactive agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, (e.g., TAXOL® by Bristol-Myers Squibb Co., Stamford, Conn.), docetaxel (e.g., Taxotere®, from Aventis S.A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include aspirin, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), coichicine, proteins, peptides, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate agents include cisplatin, insulin sensitizers, receptor tyrosine kinase inhibitors, carboplatin, alpha-interferon, genetically engineered epithelial cells, steroidal anti-inflammatory agents, non-steroidal anti-inflammatory agents, antivirals, anticancer drugs, anticoagulant agents, free radical scavengers, estradiol, antibiotics, nitric oxide donors, super oxide dismutases, super oxide dismutases mimics, 4-amino-2,2',6,6'-tetramethylpiperidine-1-oxyl (4-amino-TEMPO), tacrolimus, dexamethasone, ABT-578, clobetasol, cytostatic agents, prodrugs thereof, co-drugs thereof, and a combination thereof. Other therapeutic substances or agents may include rapamycin and structural derivatives or functional analogs thereof, such as 40-O-(2-hydroxy)ethyl-rapamycin (known by the trade name of EVEROLIMUS), 40-O-(3-hydroxy)propyl-rapamycin, 40-O-[2-(2-hydroxy)ethoxy]ethyl-rapamycin, and 40-O-tetrazole-rapamycin.

A non-polymer substrate of the device may be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

Embodiments of the devices described herein may be illustrated by a stent. FIG. 1 depicts an example of a three-dimensional view of a stent 10. The stent may be made up of a pattern of a number of interconnecting structural elements or struts 15. The embodiments disclosed herein are not limited to stents or to the stent pattern illustrated in FIG. 1. The embodiments are easily applicable to other patterns and other devices. The variations in the structure of patterns are virtually unlimited.

Additionally, a surface of an implantable medical device may also be characterized by the relative location of the surface with respect to a bodily lumen. The device may include luminal surfaces or inner portions, abluminal surfaces or outer portions, and surfaces between the luminal and abluminal surfaces or side-wall surfaces. For example, struts 15 of stent 10 include luminal surfaces 35, abluminal surfaces 40, and side-wall surfaces 45. A strut may also be described by axes, a longitudinal axis and a latitudinal axis. FIG. 2 depicts a planar projection of an abluminal or luminal surface 52 of a portion 50 of a strut depicting a longitudinal axis 55 and a latitudinal axis 60 along a straight section of portion 50. A longitudinal axis 65 on a curved section of a strut may be defined as a tangent to a curvature at a location on the curved section. A corresponding latitudinal axis 70 is perpendicular to longitudinal axis 65.

FIG. 3 depicts a three-dimensional cut-out portion 80 of a structural element or strut from a stent. Portion 80 illustrates an abluminal surface 85 and a side-wall surface 90. The luminal surface and an opposing side-wall surface are hidden. A cross-section 95 of portion 80 is rectangular with rounded corners 100. Portion 80 is shown only for the purpose of illustrating the embodiments described herein. The embodiments are not limited to the particular geometry of portion 80 and are easily applicable to other strut geometries. The cross-section of a structural element may have sharp corners that sharply delineate an edge or boundary between abluminal/luminal surfaces and side-wall surfaces. In addition, virtually any cross-sectional shape is applicable, for example, circular, square, elliptical, trapezoidal, etc.

As indicated above, a drug delivery coating for a stent with a structural element like that depicted in FIG. 3 may be designed to meet several criteria including mechanical integrity (e.g., adhesion), controlled release of the drug, and biocompatibility. Coating configurations designed to meet these criteria can include any number and combination of layers. In some embodiments, the coatings may include one or a combination of the following four types of layers:

(a) a primer layer, which may improve adhesion of subsequent layers on the implantable substrate or on a previously formed layer;

(b) a reservoir or agent layer, which may include a polymer and an agent or, alternatively, a polymer free agent;

(c) a topcoat layer, which may serve as a way of controlling the rate of release of an agent from a reservoir layer; and (d) a biobeneficial or biocompatible finishing layer containing a biobeneficial agent, which may improve the biocompatibility of the coating.

The reservoir layer can be applied directly to at least a part of a surface of an implantable medical device as a pure agent to serve as a reservoir for at least one active agent. The agent can be combined with a biodegradable polymer as a matrix, wherein the agent may or may not be bonded to the polymer. The primer layer can be applied between the surface of the device and the agent layer to improve adhesion of the agent layer to the surface or between layers and can optionally include an agent. A layer of pure or substantially pure active agent can be sandwiched between layers including biodegradable polymer. For example, it has been observed that a reservoir layer containing principally EVEROLIMUS has very poor adhesion to metallic struts. A primer layer, including, for example, poly(butyl methacrylate) (PBMA) enables an EVEROLIMUS reservoir layer to remain on the stent. The topcoat layer can be applied over at least a portion of the reservoir layer to serve as a membrane to control the rate of release of the active agent and can optionally comprise an agent.

The biobeneficial finishing layer can also be applied to increase the biocompatibility of the coating by, for example, increasing acute hemocompatibility and can also include an active agent. A "biobeneficial agent" is an agent linked to a polymer that provides a biological benefit within a mammal without necessarily being released from the polymer. A biological benefit may be that the polymer or coating is modified with the biobeneficial agent to be non-thrombogenic, such that protein absorption is inhibited or prevented to avoid formation of a thromboembolism; to promote healing, such that endothelialization of the luminal stent surfaces is rapid and forms a healthy and functional endothelial layer; or to be non-inflammatory, such that the biobeneficial agent acts as a biomimic to passively avoid attracting monocytes and neutrophils, which leads to the cascade of events creating inflammation. The biobeneficial agent can also be combined, mixed or blended with a polymer. Representative examples of biobeneficial agents include, but are not limited to, poly(alkylene glycols), poly(N-vinyl pyrrolidone), poly(acrylamide methyl propane sulfonic acid), poly(styrene sulfonate), sulfonated dextran, polyphosphazenes, poly(orthoesters), poly(tyrosine carbonate), hyaluronic acid, heparin and any derivatives, hirudin, analogs, homologues, congeners, salts, copolymers and combinations thereof.

Coating configurations on stents with one or more of the above types of layers are typically conformal, which is a coating that covers all or most of the surfaces of the struts, including the abluminal surface, luminal surface, and side-wall surfaces. FIG. 4 illustrates an exemplary conformal drug delivery coating. A cross-section 110 of a strut 115 from a stent is depicted in FIG. 4. Strut 115 has a multilayer coating on all four of its surfaces, an abluminal surface 120, luminal surface 125, and both side surfaces 130. The multilayer coating has an innermost primer layer 135 below a reservoir layer 140. A topmost layer is a topcoat layer 145 for controlling the release of active agent or drug from reservoir layer 140. Active agent may also be incorporated into topcoat layer 145 to modulate the initial release rate of active agent or to reduce sticking of the topcoat layer to a catheter balloon during delivery and deployment of a stent.

It would be desirable to have a drug delivery coating restricted completely or substantially to an abluminal surface of a stent that also addresses one or more of the criteria discussed above including mechanical integrity, controlled release, and biocompatibility. There are several advantages of having a drug delivery coating restricted completely to an abluminal surface region of a strut. From a therapeutic standpoint, an abluminal coating can be as efficacious as a conformal coating. Furthermore, an abluminal coating allows a reduction in the total polymer load on a stent, which may improve the biocompatibility of the stent. A lower polymer loading reduces the form factor of the stent which reduces the disturbance of the local blood flow, and hence, the thrombogenecity of the stent. Additionally, a decreased polymer load for biodegradable coatings reduces the likelihood of embolization due to particles of degrading polymer in the blood stream.

Another advantage of a coating restricted completely or substantially to the abluminal surface is that interactions between a topcoat layer and the catheter balloon are reduced or eliminated. It has been observed that use of an outermost topcoat layer, in particular poly(ester amide), on a luminal stent surface can have a detrimental impact on a stent's deliverability and coating mechanical integrity. The PEA coating changes the coefficient of friction between the stent and the delivery balloon. Additionally, some PEA polymers have structures that cause them to be sticky or tacky. If the PEA either increases the coefficient of friction or adheres to the catheter balloon, the smooth release of the stent from the balloon after deflation is compromised. PEA stent coatings have been observed to exhibit extensive balloon shear damage post-deployment as well, which could increase the thrombogenicity of the luminal stent surface.

The abluminal, multilayer coating configurations described herein possess the advantages discussed above and meet one or more of the criteria of mechanical integrity, controlled release, and biocompatibility. Additionally, the coatings allow controlled release from an abluminal reservoir layer without the use of reservoirs embedded in cavities or indentations in the abluminal surface. The surfaces of the structural members of the implantable medical devices used for conformal coatings are identical to those used in the presently described abluminal coating embodiments.

Embodiments of polymer coatings are illustrated by FIGS. 5-15A-B. The figures have not been drawn to scale, and the thickness of the various layers have been over or under emphasized for illustrative purposes. The polymers used for the primer material should have a high capacity of adherence to the surface of an implantable device, such as a metallic surface of a stent, or a high capacity of adherence to a polymeric surface such as the surface of a stent made of polymer, or a previously applied layer of polymeric material. The polymer in primer layers may be a homopolymer, copolymer, terpolymer, etc. The polymer may also include random, alternating, block, cross-linked, blends, and graft variations thereof. For instance, a primer layer may include PEA, poly (butyl methacrylate), or a poly(lactic acid). The active agent may be, for example, 40-O-(2-hydroxy)ethyl-rapamycin, known by the trade name of EVEROLIMUS, available from Novartis as Certican™. The active agent may be dispersed in a polymer such as poly(vinylidene fluoride-co-hexafluoropropene) (Solef). A topcoat or barrier layer may be any polymer that controls the migration of active agent. For example, the topcoat layer may include PEA.

By way of example, and not limitation, a primer layer can have any suitable thickness, examples of which can be in the range of about 0.1 to about 10 microns, or more narrowly about 0.1 to about 2 microns. A reservoir layer can have a thickness of about 0.1 microns to about 20 microns, or more narrowly about 0.5 microns to 15 microns. The amount of the active agent to be included on an implantable medical device can be further increased by applying a plurality of reservoir layers on top of one another. A topcoat layer can have any suitable thickness, examples of which can be in the range of about 0.1 to about 20 microns, or more narrowly about 0.1 to about 10 microns.

"Above" a surface or layer is defined as higher than or over a surface or layer measured along an axis normal to a surface, but not necessarily in contact with the surface or layer. "Below" is defined as the opposite of "above." "Cover" is defined as above and in contact with. "Continuous" is defined as marked by uninterrupted extension in space. As used herein, an "edge" of a layer refers to a line or region on a surface delineating where the layer ends.

A structural element of an implantable medical device, such as a stent, suitable for coating embodiments disclosed herein may include a surface having an abluminal side, a luminal side, and two sidewalls extending between the abluminal side and the luminal side. Several embodiments include coating layers above the abluminal side, and optionally over a minor portion of one or both of the sidewalls adjacent to the abluminal side. Some of these abluminal or substantially abluminal coating embodiments include controlled release of active agents from a reservoir layer and/or improved adhesion due to primer layer(s). In the embodiments of the coatings described below, the surface of the structural element below the coating is cavity free.

One embodiment of a coating on a structural element of an implantable medical device may include a continuous first layer disposed above a majority of the abluminal side. The continuous first layer may optionally be above a portion of at least one of the side-walls extending from the abluminal side. The luminal side and portions of the sidewalls may be free from the first layer.

The coating may further include a continuous second layer covering the first layer such that no portion of the first layer is not covered by the second layer. The luminal side of the structural element may be free from the second layer. In some embodiments, the second layer may cover a portion of the structural element not covered by the first layer. In one embodiment of the coating, a majority of the sidewalls may be free from the first layer and the second layer.

It may be advantageous to have a third layer above the reservoir layer that may function as a topcoat layer, primer layer, and/or biobeneficial layer. A topcoat layer may control the release of active agent from the reservoir layer. Additionally, a third layer functioning as a primer layer may improve the adhesion between a second layer and another layer above the second layer. In some embodiments, a continuous third layer may cover the second layer such that no portion of the second layer is not covered by the third layer. Additionally, the third layer may cover a portion of the structural element not covered by the second layer.

In one embodiment, a majority of the sidewalls may be free from the third layer. Alternatively, the third layer may cover a portion of or all of the sidewalls.

In a further embodiment, the luminal side of the structural element may be free from the third layer. Alternatively, the third layer may cover a portion of or the entire luminal side.

In certain embodiments, at least one of the first or second layers may be a reservoir layer that includes a pure or substantially pure active agent. In one such embodiment, the first layer may be a reservoir layer. In this embodiment, the second layer may be a topcoat or barrier layer that functions to control the release of active agent from the reservoir layer. The second layer may additionally or alternatively function as a primer layer that improves adhesion between the reservoir layer and another layer above the second layer.

FIG. 5 is a cross-sectional view of an embodiment of an abluminally coated structural element 150. Structural element 150 has a coating with a reservoir layer 155 above a portion 160 of an abluminal surface 162. The coating also includes a second layer 170 above reservoir layer 155 and two additional portions 175 of the surface not below first layer 155. Additional portions 175 are adjacent to edges 190 of reservoir layer 155. Furthermore, additional portions 175 include a portion of abluminal surface 162 and sidewall surfaces 180 since edges 195 of second layer 170 lie on side-wall surfaces 180. A majority of the sidewall surfaces 180 and all of a luminal surface 185 are free of reservoir layer 155 and second layer 170. As indicated above, second layer 170 may be a topcoat or barrier layer. In this case, the topcoat layer effectively seals in the reservoir layer and controls the release rate of an active agent from reservoir layer 155.

Figure 6:
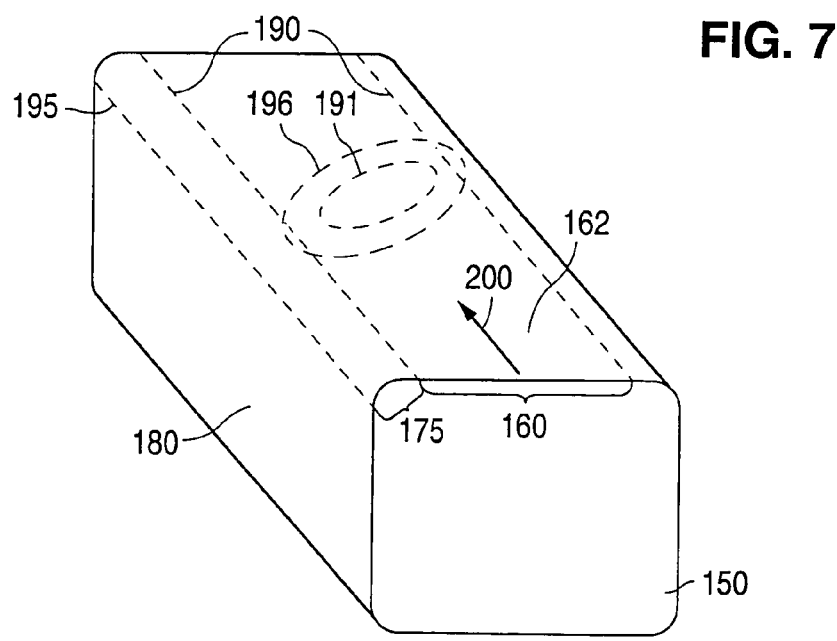
FIG. 6 depicts a three-dimensional view showing the edges of coating layers illustrated in FIG. 5.

In certain embodiments, coating layers in an abluminal or substantially abluminal coating may be strip-shaped with at least one edge of a coating layer parallel to a longitudinal axis of the structural element. As an illustration, FIG. 6 depicts a three-dimensional rendering of a portion of structural element 150 illustrating embodiments of coating layers of the coating shown in FIG. 5. FIG. 6 illustrates a strip-shaped reservoir layer 155 and strip-shaped second layer by showing the outline of edges 190 of reservoir layer 155 and edges 195 of second layer 170. Edges 190 and 195 are parallel to a longitudinal axis 200 of structural member 150. In other embodiments, an abluminal or substantially abluminal coating may have any useful shape, for example, disc-shaped, rectangular, etc. FIG. 6 also depicts reservoir layer 155 and second layer 170 as disc-shaped with edges 191 and 196, respectively.

Figure 7:
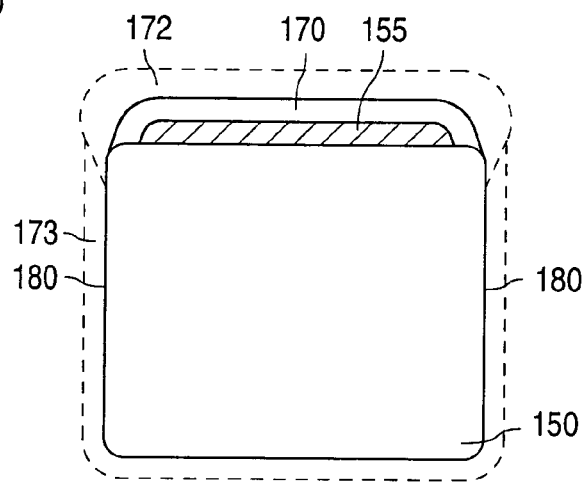
FIG. 7 depicts the coating embodiment in FIG. 5 with a biobeneficial layer.

FIG. 7 illustrates the use of a biobeneficial layer with the coating configuration from FIG. 5. In FIG. 7, a biobeneficial layer 172 is shown covering all of second layer 170 and a portion of sidewall 180. An alternative biobeneficial layer 173 is also shown that covers all of second layer 170 and the remaining portion of the surface of the structural member 150.

In alternate embodiment, the second layer may be a reservoir layer. In this embodiment, the first layer may then be primer layer that improves adhesion between a reservoir layer and a surface or another layer.

Figure 8:
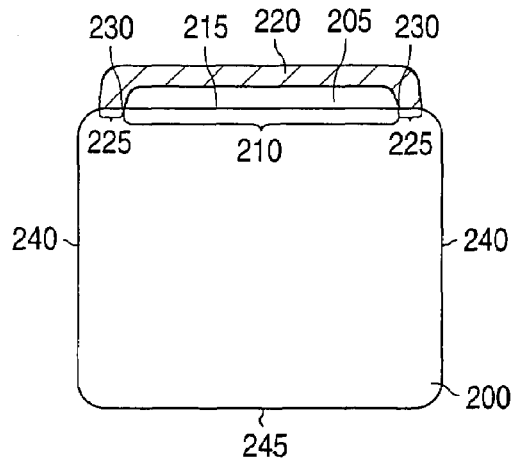
FIG. 8 depicts a cross-sectional view of an embodiment of an abluminally coated structural element of a stent.

FIG. 8 is a cross-sectional view of an embodiment of a structural member 200 having a coating with a primer layer 205 above a portion 210 of an abluminal surface 215. The coating also includes a reservoir layer 220 above primer layer 205 and two additional portions 225 of the surface not below primer layer 205. Additional portions 225 are adjacent to edges 230 of primer layer 205. All of the side-wall surfaces 240 and a luminal surface 245 are not below primer layer 205 and reservoir layer 220.

Figure 9:
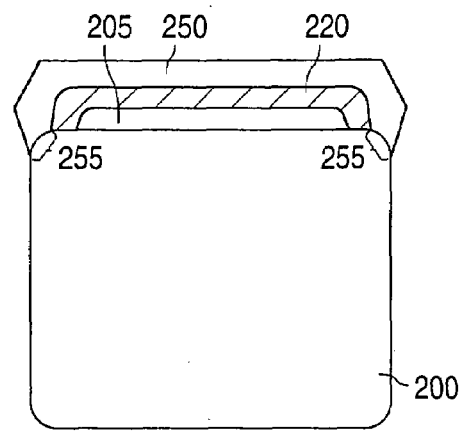
FIG. 9 depicts the coating embodiment illustrated in FIG. 8 with a third layer.

As discussed above, it may be advantageous to have third layer above the reservoir layer that functions as a topcoat and/or biobeneficial layer. FIG. 9 depicts the coating illustrated in FIG. 8 with a third layer 250 above reservoir layer 220. Third layer 250 covers reservoir layer 220 and portions 255 of the surface of structural member 200. The structural member may further include a fourth layer, for example, a biobenefical layer covering the third layer and a portion or the entire surface not below the other third layer.

Other embodiments of a coating on a structural element may include a continuous first layer disposed above a majority of the abluminal side of the structural element and optionally above a portion of at least one of the side-walls extending from the abluminal side. The luminal side and portions of the sidewalls may be free from the first layer. The coating may also include a continuous second layer covering a portion of the first layer such that at least a portion of the first layer is not covered by the second layer. A majority of the sidewalls may be free from the first layer and the second layer. In an embodiment, the second layer may be a reservoir layer and the first layer may be a primer layer that improves adhesion of the reservoir layer to the surface of the structural element.

Figure 10:
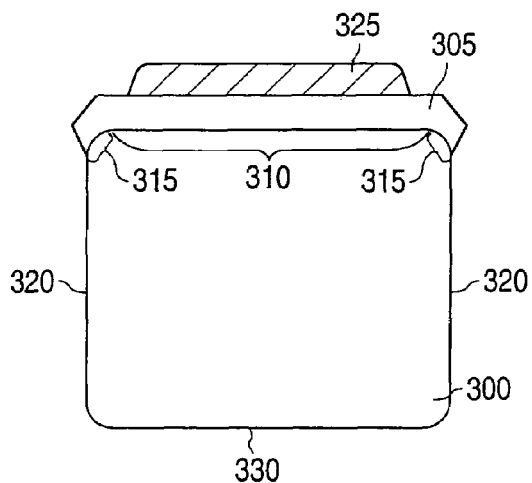
FIG. 10 depicts a cross-sectional view of an embodiment of an abluminally coated structural element of a stent.

FIG. 10 is a cross-sectional view of an embodiment of a coated structural element 300. Structural element 300 has a coating with a primer layer 305 above an abluminal surface 310 and portions 315 of sidewall surfaces 320. The coating also includes a reservoir layer 325 above a portion of primer layer 305. Most of the side-wall surfaces 320 and the entire luminal surface 330 are free of the primer layer 305 and reservoir layer 325.

Additionally, an embodiment exemplified in FIG. 10 may further include a third layer above the reservoir layer, which may function as a topcoat layer, primer layer, and/or biobeneficial layer. The third layer may be a continuous layer covering the second layer such that no portion of the second layer is not covered by the third layer. In some embodiments, a third layer may be above a portion, but not the entire first layer. Alternatively, the third layer may be above the entire first layer. In addition, the third layer may cover the entire first layer and a portion of the surface of the structural element not covered by the first layer. In one embodiment, a majority of the sidewalls may be free from the third layer.

Figure 11:
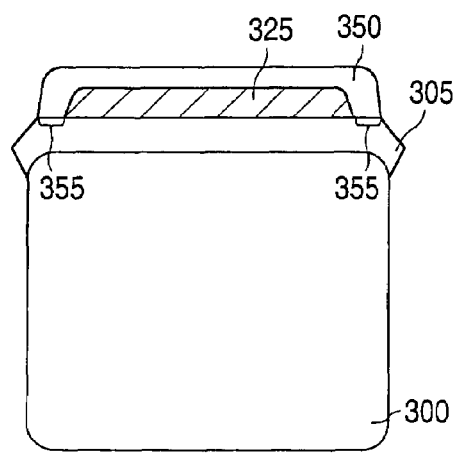
FIG. 11 depicts the coating embodiment illustrated in FIG. 10 with a third layer.

FIG. 11 depicts the coating illustrated in FIG. 10 with a third layer 350 above reservoir layer 325. Third layer 350 covers reservoir layer 325 and portions 355 of primer layer 305.

The structural member may further include a fourth layer covering the third layer such that no portion of the third layer is not covered by the fourth layer. The fourth layer may be a biobeneficial coating layer that increases biocompatibility of the coating.

Furthermore, numerous variations of the coating embodiments described above are possible. Such variations may be configured to achieve release control of active agent from a reservoir layer, improve adhesion between layers, and/or improve biocompatibility of the coating. In certain embodiments, abluminal or substantially abluminal coating embodiments may have multiple primer and reservoir layers with the layers alternating between the two types of layers through the thickness of the coating. Such embodiments may be useful, for example, for a course of treatment that occurs in stages where each stage requires the use of a different type or types of active agents.

Moreover, multiple primer and reservoir embodiments may utilize the release control topcoat-reservoir embodiment exemplified in FIG. 5 and the adhesion improvement primer-reservoir embodiments exemplified in FIGS. 8 and 10. FIG. 8 exemplifies an embodiment in which a reservoir layer is above a portion of the primer layer and a portion of the surface not below the primer layer. FIG. 10 exemplifies an embodiment in which a reservoir layer is above a portion of the primer layer.

Figure 12:
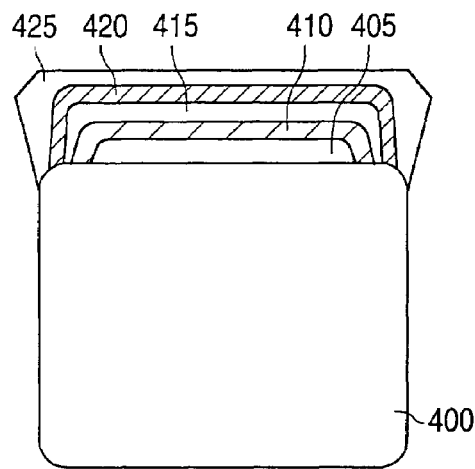
FIG. 12 depicts a multiple primer and reservoir layer coating with repeat units of the embodiment exemplified in FIG. 8.

One embodiment of a multiple primer and reservoir layer coating may include repeat units of the embodiment exemplified in FIG. 8. FIG. 12 illustrates such a multilayer embodiment. FIG. 12 depicts structural element 400 with a first primer layer 405, a first reservoir layer 410, a second primer layer 415, and a second reservoir layer 420. A topcoat layer 425, for controlling the release of active agent from first reservoir layer 410 and second reservoir layer 420, is also shown. Second primer layer 415 may also act to control the release of active agent form first reservoir layer 410. The combination of second reservoir layer 420 and topcoat layer 425 utilizes the embodiment exemplified in FIG. 5.

Figure 13:
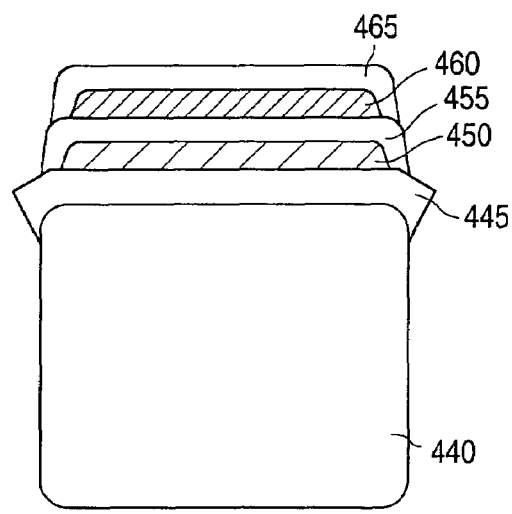
FIG. 13 depicts a multiple primer and reservoir layer coating with repeat units of the embodiment exemplified in FIG. 10.

Another embodiment of a multiple primer and reservoir layer coating may include repeat units of the embodiment exemplified in FIG. 10. FIG. 13 illustrates such an embodiment. FIG. 13 depicts structural element 440 with a first primer layer 445, a first reservoir layer 450, a second primer layer 455, and a second reservoir layer 460. A topcoat layer 465, for controlling the release of active agent from first reservoir layer 450 and second reservoir layer 460, is also shown. Second primer layer 455 may also act to control the release of active agent from first reservoir layer 450.

Figure 14A:
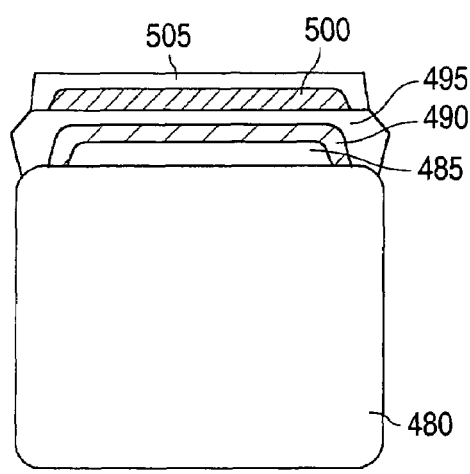
FIG. 14A depicts a multiple primer and reservoir layer coating with the embodiment exemplified in FIG. 8 below the embodiment exemplified in FIG. 10.

A further embodiment of a multiple primer and reservoir layer coating may include the embodiment exemplified in FIG. 8 below the embodiment exemplified in FIG. 10. FIG. 14A depicts structural element 480 with a first primer layer 485, a first reservoir layer 490, a second primer layer 495, and a second reservoir layer 500. A topcoat layer 505, for controlling the release of active agent from first reservoir layer 490 and second reservoir layer 500, is also shown. Second primer layer 495 may also act to control the release of active agent from first reservoir layer 490.

Figure 14B:
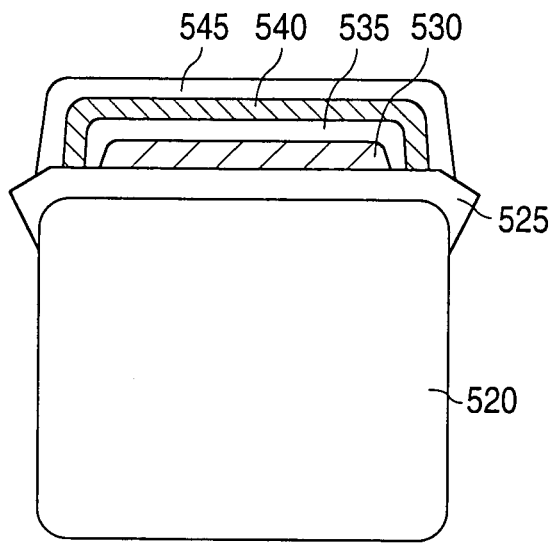
FIG. 14B depicts a multiple primer and reservoir layer coating with the embodiment exemplified in FIG. 10 below the embodiment exemplified in FIG. 8.

Additionally, the embodiment exemplified in FIG. 10 may be below the embodiment exemplified in FIG. 8. FIG. 14B depicts structural element 520 with a first primer layer 525, a first reservoir layer 530, a second primer layer 535, and a second reservoir layer 540. A topcoat layer 545, for controlling the release of active agent from first reservoir layer 530 and second reservoir layer 540, is also shown. Second primer layer 535 may also act to control the release of active agent from first reservoir layer 530.

Figure 15A:
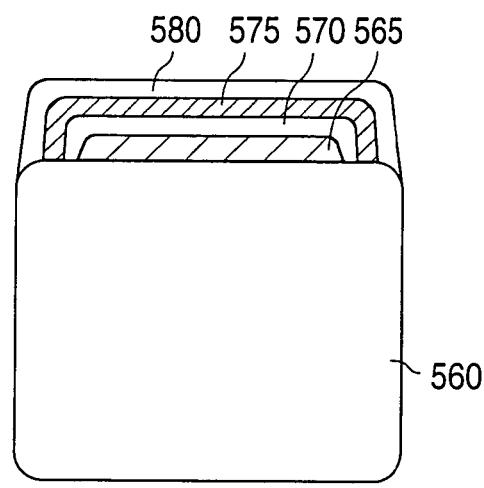
FIG. 15A depicts a coating that includes the coating of FIG. 5 below the embodiment exemplified by FIG. 8.

In addition, a multiple primer and reservoir coating may include the coating shown in FIG. 5, with topcoat layer 170 acting as a primer layer, combined with the embodiments exemplified by FIGS. 8 and/or FIG. 10. FIG. 15A illustrates a coating that includes the coating of FIG. 5 below the embodiment exemplified by FIG. 8. FIG. 15A depicts structural element 560 with a first reservoir layer 565, a first primer layer 570, and a second reservoir layer 575. A topcoat layer 580, for controlling the release of active agent from first reservoir layer 565 and second reservoir layer 575, is also shown.

Figure 15B:
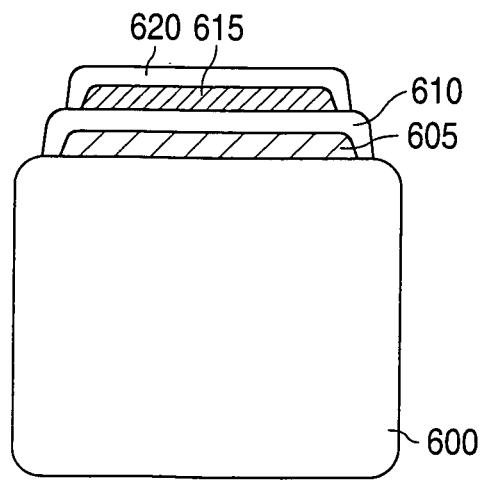
FIG. 15B depicts a coating that includes the coating of FIG. 5 below the embodiment exemplified by FIG. 10.

Additionally, FIG. 15B illustrates a coating that includes the coating of FIG. 5 below the embodiment exemplified by FIG. 10. FIG. 15B depicts structural element 600 with a first reservoir layer 605, a first primer layer 610, and a second reservoir layer 615. A topcoat layer 620, for controlling the release of active agent from first reservoir layer 605 and second reservoir layer 615, is also shown.

Various methods may be used to form coatings as described herein including, but not limited to, ink-jet-type coating, electrostatic coating, roll coating, thermal deposition with masking, plasma polymerization with masking, direct application of polymer/solvent solution by micro-syringe, direct polymer melt application, and spray coating with photomasking. For example, a controlled deposition system ink-jet-type coating method can be used that applies various substances only to certain targeted portions of an implantable medical device. A representative example of such a system, and a method of using the same, is described in U.S. Pat. No. 6,395,326 to Castro et al. A controlled deposition system can be capable of depositing a substance on an implantable medical device having a complex geometry, and otherwise apply the substance so that coating is limited to particular portions of the device. The system can have a dispenser and a holder that supports the medical substrate. The dispenser and/or holder can be capable of moving in very small intervals, for example, less than about 0.001 inch. Furthermore, the dispenser and/or holder can be capable of moving in the x-, y-, or z-direction, and be capable of rotating about a single point.

The controlled deposition system can include a dispenser assembly. The dispenser assembly can be a simple device including a reservoir, which holds a composition prior to delivery, and a nozzle having an orifice through which the composition is delivered. One exemplary type of dispenser assembly can be an assembly that includes an ink-jet-type printhead. Another exemplary type of a dispenser assembly can be a microinjector capable of injecting small volumes ranging from about 2 to about 70 nL, such as NanoLiter 2000 available from World Precision Instruments or Pneumatic PicoPumps PV830 with Micropipette available from Cell Technology System. Such microinjection syringes may be employed in conjunction with a microscope of suitable design.

Furthermore, selective coating of an implantable medical device may be performed using photomasking techniques. Deposition and removal of a mask can be used to selectively coat surfaces of substrates. Masking deposition is known to one having ordinary skill in the art.

Additionally, the substances of the present invention can also be selectively deposited by an electrostatic deposition process. Such a process can produce an electrically charged or ionized coating substance. The electric charge causes the coating substance to be differentially attracted to the device, thereby resulting in higher transfer efficiency. The electrically charged coating substance can be deposited onto selected regions of the device by causing different regions of the device to have different electrical potentials.

FIGS. 16-20 illustrate examples of the use of electrostatic coating to coat a stent. FIGS. 16-20 depict scanning electron micrograph (SEM) images of stents with poly(ester amide) (PEA) coatings. The stent used in the examples is a metallic Vision stent obtained from Guidant Corporation in Santa Clara, Calif. The stents had a 3 mm outside diameter and were 12 mm in length.

Figure 16:
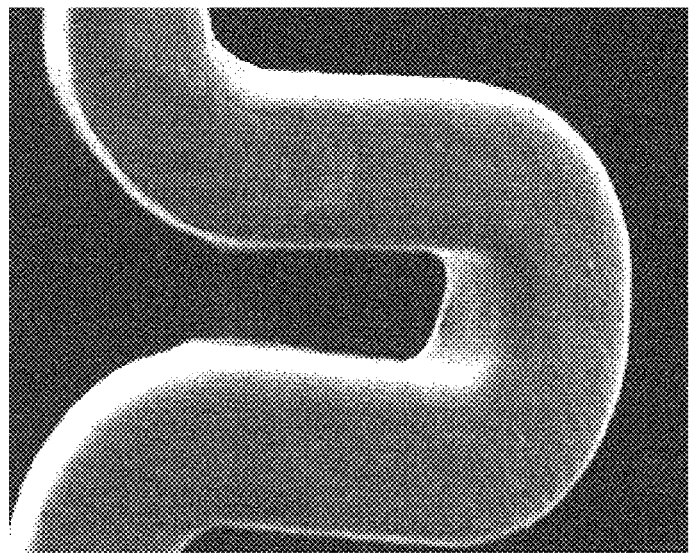
FIG. 16 depicts an SEM image of an abluminal surface of an electrostatically coated stent after wet expansion.
Figure 17:
FIG. 17 depicts an SEM image of a luminal surface of an electrostatically coated stent after wet expansion.
Figure 18:
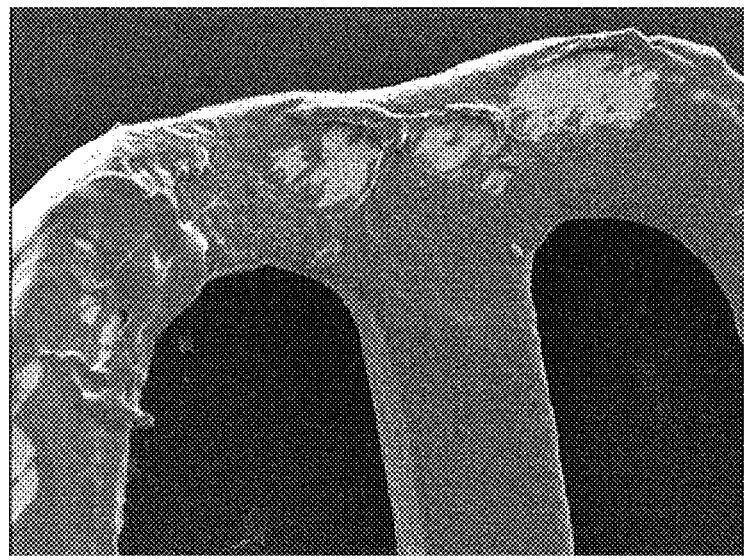
FIG. 18 depicts an SEM image of a luminal surface of an electrostatically coated stent after wet expansion.

An electrostatic coating method was used to coat the stent with a total solid of 328 μg using a 2% by weight solution of PEA-TEMPO in ethanol. PEA-TEMPO may be obtained from Guidant Corporation. The stent was translated and rotated under an electrospray nozzle. A different electrical potential on the luminal and abluminal surfaces was created by using a plastic sleeve over a spray mandrel. The plastic sleeve repelled the same charged droplets which prevented the droplets from depositing onto the luminal side of the stent. This resulted in a thinner coating layer on the luminal surface than the abluminal surface. A syringe pump was controlled at 1 cc/hr, and voltage was set at 5 kV. The coated stent was oven dried at 50° C. for 30 minutes. FIG. 16 depicts an SEM image of an abluminal surface of the stent after wet expansion of the stent using a catheter balloon with an outside diameter of 3.5 mm. The coating is intact, as shown by the image. FIGS. 17 and 18 depict the luminal surfaces of the stent after the wet expansion. The thin layer of coating in FIGS. 17 and 18 exhibits minor to moderate balloon shear damage.

Figure 19:
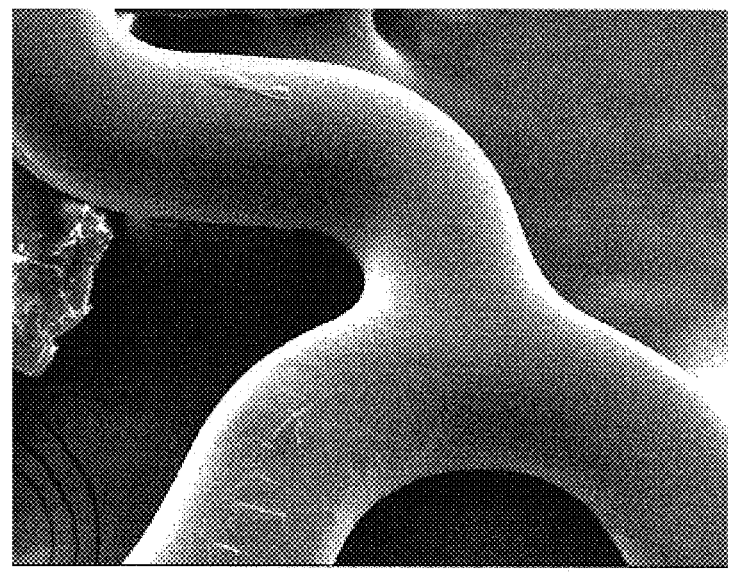
FIG. 19 depicts an SEM image of a luminal surface of a conventionally coated stent after dry expansion.
Figure 20:
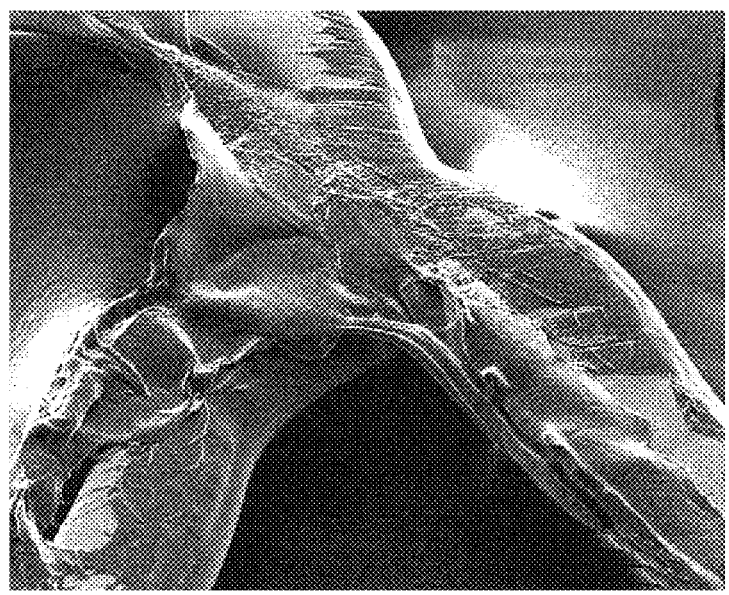
FIG. 20 depicts an SEM image of a luminal surface of a conventionally coated stent after wet expansion.

Another of the same type of stent was coated using conventional spray coating to compare with the electrostatically coated stent. The stent was coated with 300 μg of 2% by weight solution of PEA-TEMPO in ethanol. The coated stent was oven dried at 50° C. for 30 minutes. FIG. 19 depicts a luminal surface after dry expansion with a catheter balloon of the conventionally coated stent to an outside diameter of 3.33 mm. FIG. 19 shows a thicker coating than what is obtained using electrostatic coating (see FIGS. 17 and 18). FIG. 20 shows the luminal surface of the conventionally coated stent after wet expansion with a catheter balloon with an outside diameter of 3.3 mm. FIG. 20 shows extensive balloon shear damage to the thicker PEA-TEMPO coating. The damage to the coating was much more extensive than the electrostatically applied coating (see FIGS. 17 and 18).

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A structural element of an implantable medical device, a surface of the structural element comprises an abluminal side, a luminal side, and two sidewalls extending between the abluminal side and the luminal side, wherein the structural element has a coating comprising:
a continuous first layer disposed above all or a majority of the abluminal side and above a portion of at least one of the sidewalls extending from the abluminal side, wherein the luminal side and other portions of the at least one sidewall are free from the first layer wherein the first layer comprises a polymer; and
a continuous second layer covering the first layer such that no portion of the first layer is not covered by the second layer, and wherein the luminal side of the structural element is free from the second layer;
wherein the second layer covers a portion of the structural element not covered by the first layer,
wherein the first layer is over the portion of the at least one of the sidewalls measured along an axis normal to the portion of the at least one of the sidewalls.

2. The structural element of claim 1, wherein a majority of the sidewalls are free from the first layer and the second layer.

3. The structural element of claim 1, wherein the structural element comprises a second polymer.

4. The structural element of claim 3, wherein the second polymer is biodegradable.

5. The structural element of claim 3, wherein the second polymer is poly(ester amide).

6. The structural element of claim 1, wherein the implantable medical device is a stent.

7. The structural element of claim 1, wherein the structural element comprises a metal.

8. The structural element of claim 1, wherein at least one of the layers is a reservoir layer comprising a substance selected from the group consisting of rapamycin, 40-O-(2-hydroxy)ethyl-rapamycin, 40-O-(3-hydroxy)propyl-rapamycin, 40-O-[2-(2-hydroxy)ethoxy]ethyl-rapamycin, 40-O-tetrazole-rapamycin, and a combination thereof.

9. The structural element of claim 1, wherein the second layer is a reservoir layer comprising a pure or substantially pure active agent.

10. The structural element of claim 1, wherein the first layer comprises an active agent dispersed and/or dissolved in the polymer.

11. The structural element of claim 1, wherein the polymer is biodegradable.

12. The structural element of claim 1, wherein the first layer comprises a reservoir layer, and wherein the second layer comprises a topcoat layer, primer layer, and/or biobeneficial layer.

13. The structural element of claim 1, wherein the first layer comprises a topcoat layer, primer layer, and/or biobeneficial layer, and wherein the second layer comprises a reservoir layer.

14. The structural element of claim 1, wherein the second layer comprises poly(ester amide).

15. The structural element of claim 1, wherein the first layer and/or the second layer are strip-shaped such that at least one edge of the first layer and/or at least one edge of the second layer is parallel or substantially parallel to a longitudinal axis of the structural element.

16. The structural element of claim 1, further comprising a continuous third layer covering the second layer such that no portion of the second layer is not covered by the third layer.

17. The structural element of claim 16, wherein the third layer is a biobeneficial coating layer and/or a topcoat layer.

18. The structural element of claim 16, wherein the luminal side of the structural element is free from the third layer.

19. The structural element of claim 16, wherein a majority of the sidewalls are free from the third layer.

20. The structural element of claim 16, wherein the third layer comprises poly(ester amide).

21. The structural element of claim 1, wherein the second layer comprises an active agent dispersed and/or dissolved in a second polymer.

22. The structural element of claim 1, wherein a surface of the structural element below the coating is cavity free.

23. The structural element of claim 1, wherein the second layer does not entirely cover the sidewalls.

24. The structural element of claim 1, wherein the first layer contacts the portion of the at least one of the sidewalls.

25. A structural element of an implantable medical device, a surface of the structural element comprises an abluminal side, a luminal side, and two sidewalls extending between the abluminal side and the luminal side, wherein the structural element has a coating comprising:
a continuous first layer disposed above all or a majority of the abluminal side and above a portion of at least one of the sidewalls extending from the abluminal side, wherein the luminal side and other portions of the at least one sidewall are free from the first layer wherein the first layer comprises a polymer;
a continuous second layer covering the first layer such that no portion of the first layer is not covered by the second layer, and wherein the luminal side of the structural element is free from the second layer; and
a continuous third layer covering the second layer such that no portion of the second layer is not covered by the third layer;
wherein the third layer covers a portion of the structural element not covered by the second layer,
wherein the first layer is over the portion of the at least one of the sidewalls measured along an axis normal to the portion of the at least one of the sidewalls.

26. The structural element of claim 25, wherein the second and third layers do not entirely cover the sidewalls.

27. The structural element of claim 25, wherein the first layer contacts the portion of the at least one of the sidewalls.

28. A structural element of an implantable medical device, a surface of the structural element comprises an abluminal side, a luminal side, and two sidewalls extending between the abluminal side and the luminal side, wherein the structural element has a coating comprising:
a continuous first layer disposed above all or a majority of the abluminal side and above a portion of at least one of the sidewalls extending from the abluminal side, wherein the luminal side and portions of the sidewalls are free from the first layer wherein the first layer comprises a polymer;
a continuous second layer covering the first layer such that no portion of the first layer is not covered by the second layer, and wherein the luminal side of the structural element is free from the second layer;
a continuous third layer covering the second layer such that no portion of the second layer is not covered by the third layer;
a continuous fourth layer covering the third layer such that no portion of the third layer is not covered by the fourth layer; and wherein the first layer is over the portion of the at least one of the sidewalls measured along an axis normal to the portion of the at least one of the sidewalls.

29. The structural element of claim 28, wherein the first layer is disposed above a portion of at least one of the sidewalls.

30. The structural element of claim 28, wherein the second and third layers do not entirely cover the side walls.

31. A structural element of an implantable medical device, a surface of the structural element comprises an abluminal side, a luminal side, and two sidewalls extending between the abluminal side and the luminal side, wherein the structural element has a coating comprising:
   a continuous first layer disposed above all or a majority of the abluminal side and above a portion of at least one of the sidewalls extending from the abluminal side, wherein the luminal side and portions of the sidewalls are free from the first layer; and
   a continuous second layer covering a portion of the first layer such that at least a portion of the first layer is not covered by the second layer, the second layer different in composition from the first layer;
   a continuous third layer covering the second layer such that no portion of the second layer is not covered by the third layer;
   a continuous fourth layer covering the third layer such that no portion of the third layer is not covered by the fourth layer, wherein the fourth layer is a biobeneficial coating layer that increases biocompatibility of the coating; and
   wherein the first layer is over the portion of the at least one of the sidewalls measured along an axis normal to the portion of the at least one of the sidewalls.

* * * * *

UNITED STATES PATENT AND TRADEMARK OFFICE
CERTIFICATE OF CORRECTION

PATENT NO. : 7,632,307 B2  Page 1 of 1
APPLICATION NO. : 11/015313
DATED : December 15, 2009
INVENTOR(S) : Pacetti et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 317 days.

Signed and Sealed this

Twenty-first Day of December, 2010

David J. Kappos
*Director of the United States Patent and Trademark Office*